(12) United States Patent
Nadel et al.

(10) Patent No.: US 9,068,929 B2
(45) Date of Patent: Jun. 30, 2015

(54) CAPACITANCE-BASED SYSTEM HEALTH MONITORING SYSTEM, APPARATUS AND METHOD FOR LAYERED STRUCTURE

(75) Inventors: Adam Ian Nadel, Woodbridge, VA (US); Adam Scott Ehrmantraut, Manassas Park, VA (US)

(73) Assignee: Aurora Flight Sciences Corporation, Manassas, VA (US)

( * ) Notice: Subject to any disclaimer, the term of this patent is extended or adjusted under 35 U.S.C. 154(b) by 1026 days.

(21) Appl. No.: 13/159,539

(22) Filed: Jun. 14, 2011

(65) Prior Publication Data
US 2012/0319706 A1    Dec. 20, 2012

(51) Int. Cl.
*G01R 27/26* (2006.01)
*G01N 27/22* (2006.01)

(52) U.S. Cl.
CPC ...................................... *G01N 27/22* (2013.01)

(58) Field of Classification Search
USPC ............. 324/679; 257/347, 40, 253; 438/104, 438/149, 161
See application file for complete search history.

(56) References Cited

U.S. PATENT DOCUMENTS

2011/0245999 A1   10/2011   Kordonowy
2013/0240241 A1*   9/2013   Dubrow et al. ............ 174/113 R

OTHER PUBLICATIONS

Uppu, Ravitej, AC Bridges : Measuring Capacitance using de Sauty and Schering Bridges. (www.cmi.ac.in/~ravitej/lab/acbrid-capacitance.pd).
U.S. Appl. No. 13/020,195, Ehrmantraut.
ECE Lab—Schering Bridge (ecelab.com/schering-bridge.htm).Accessed Apr. 18, 2011.

* cited by examiner

*Primary Examiner* — Melissa Koval
*Assistant Examiner* — Trung Nguyen
(74) *Attorney, Agent, or Firm* — Katten Muchin Rosenman LLP

(57) ABSTRACT

The present disclosure endeavors to provide an SHM system and method using a conductive material (e.g., CNT) to measure changes in a layered structure. Change in capacitance of a layered structure may be measured over time thereby indicating a change in the structural integrity of the material. The SHM system may be embedded with, or within, the layered structure such that the system is effectively part of the material. Alternatively, it may be external to the layered structure such that the system is a separate device used to measure the capacitance. The SHM system may also localize any changes in a layered structure by using, for example, strips or panels of conductive material on opposite sides of the layered structure being measured. Damage within overlapping portions of the conductive material provides localization capability where varying the size of the strips or panels may be use to vary the sensitivity and resolution of both the locations and size of the defect.

28 Claims, 18 Drawing Sheets

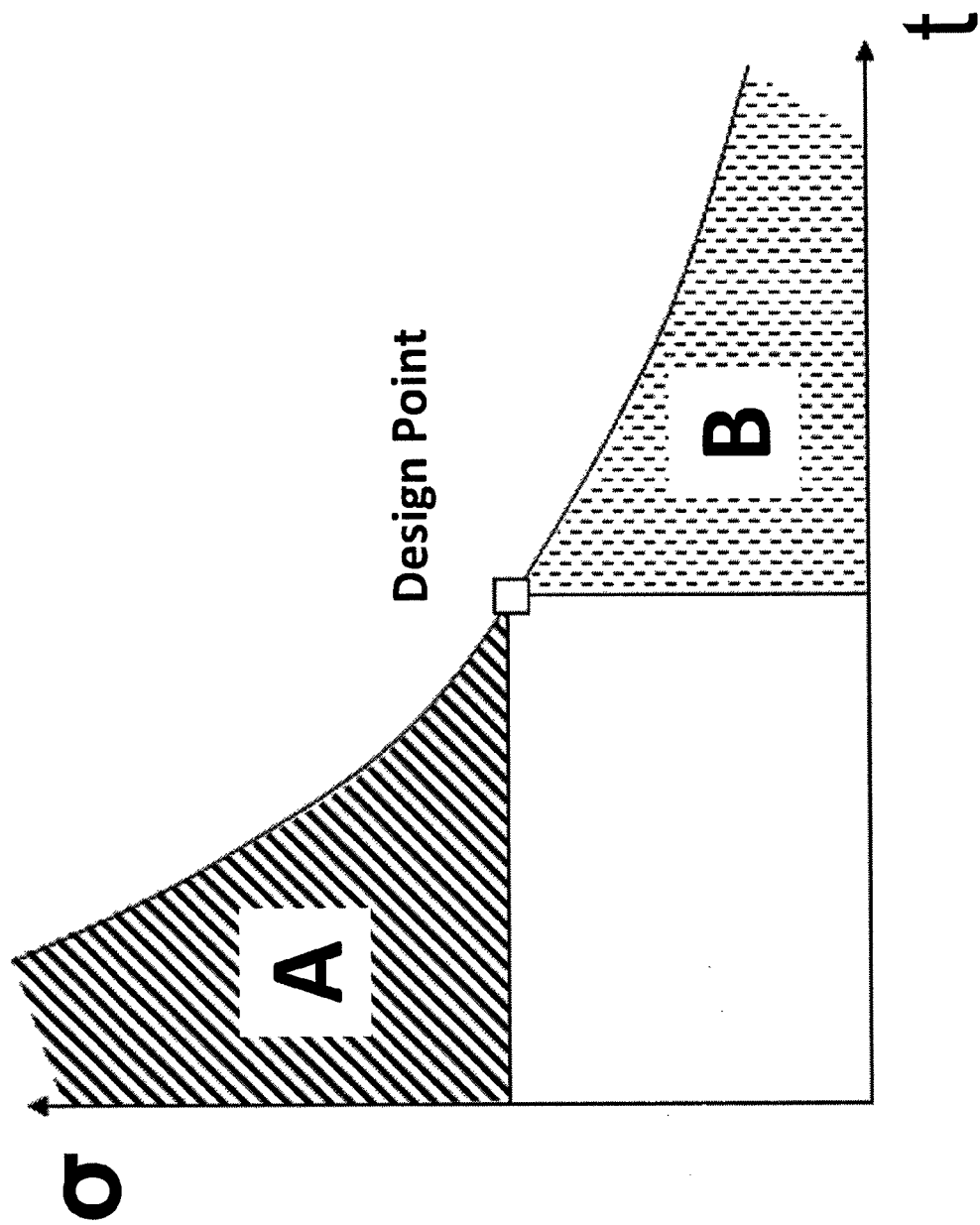

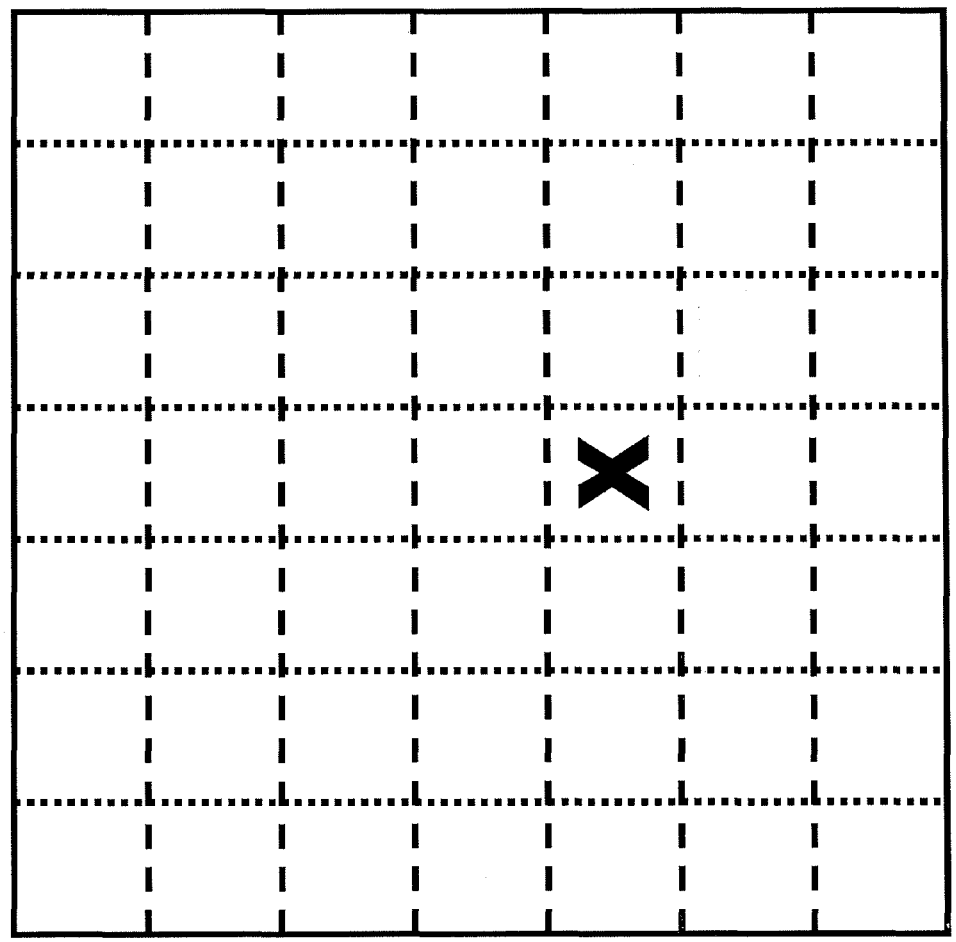
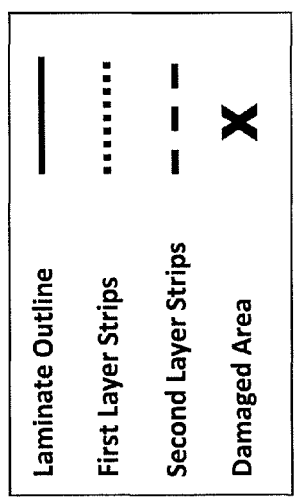
Figure 4a

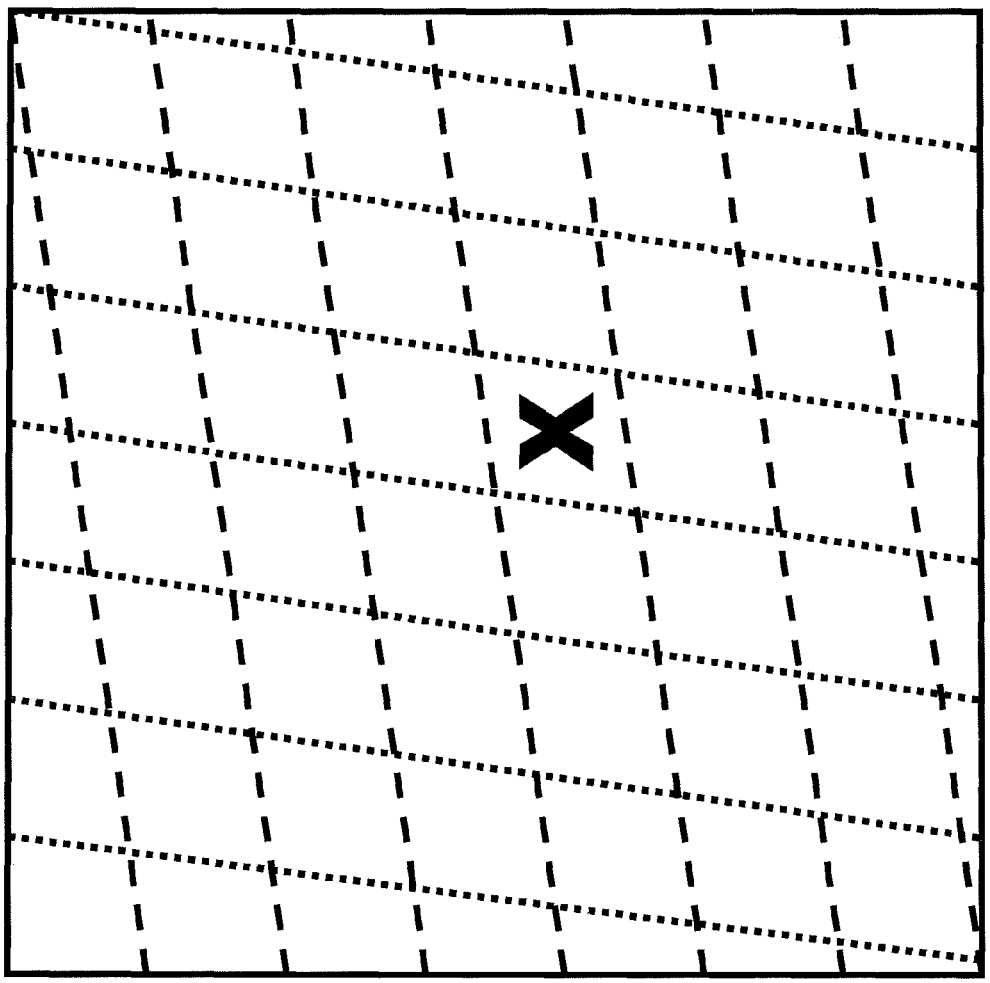
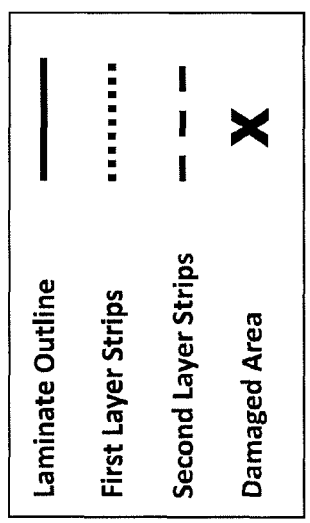
Figure 4b

CAPACITANCE-BASED SYSTEM HEALTH MONITORING SYSTEM, APPARATUS AND METHOD FOR LAYERED STRUCTURE

TECHNICAL FIELD

The present invention relates to structural health monitoring ("SHM"). More particularly, the invention relates to structural health monitoring using capacitance measurement techniques and a conductive material (e.g., carbon nanotubes, copper, etc.) to detect and measure changes in a vehicle structure.

BACKGROUND INFORMATION

Compared to earlier systems, modern airborne systems push the limits of technology to achieve greater speed, payload, and efficiency. To accomplish these objectives, advanced aircraft structural designs often employ unitized bonded layered structures (e.g., resins or plastic reinforced with fibers) while former methods required that a multitude of components be joined (e.g., bolted, riveted, and/or welded) with a plurality of access points (i.e., inspection points).

In aviation, weight is a crucial factor, and removing or reducing the number of access points within a structure reduces the overall aircraft weight. While unitized bonded layered structures reduce weight, they also reduce the number of access points, creating the necessity for new maintenance and inspection strategies to compensate for the reduced number of access points. For example, as advanced layered structures become more unitized, inspection of remote and inaccessible locations for any damage caused by Foreign Object Debris (FOD) or liquid intrusion becomes increasingly difficult, sometimes impossible, while at the same time making inspection and maintenance a higher priority. Current inspection methods typically involve physically removing one or more unitized aircraft structural components to enable proper inspections and ensure that critical structures have not been damaged. However, not surprisingly, this endeavor is costly in terms of both manpower and loss of vehicle availability.

For example, in the case of the Sikorsky CH-53E Super Stallion, a heavy-lift cargo helicopter in service with the U.S. Marine Corps, up to 30-40 man-hours per flight hour may be necessary to ensure the helicopter is structurally sound. Currently, non-destructive evaluation and inspection (NDE/NDI) methods for detecting damage or liquid intrusion must be completed by touch labor (manual inspection) on and/or off the aircraft. Unfortunately, these in-depth, labor-intensive inspections also have the consequence of providing further opportunities for damage through accidents such as tool drops or FOD.

Furthermore, it is highly desirable to be able to characterize and identify material aging issues such as matrix cracking, delaminating, and water intrusion into layered panels without the need to perform detailed NDE inspections or tear-down tests that require large amounts of time, highly skilled labor, and removal of structure. More recently, aging is becoming a real concern for layered structures as early layered components are reaching service life times where the effects of aging have not yet been quantified and the remaining useful life is unknown. For instance, tear-down tests of graphite/epoxy components by the National Institute For Aviation Research (NIAR) on the Boeing 737-200 and Beechcraft Starship have shown little degradation of the structures over their respective 18- and 12-year histories. However, exposure to ultraviolet light and moisture can break down the fiber matrix bond over time, while micro-cracking can lead to stress risers at the crack tip, reducing service life. These types of issues are often precursors to failure, and detecting them prior to failure can be quite difficult. Not surprisingly, layered aerial vehicles also age in relation to overall system maintenance and inspection routines, where the probability of degraded structure increases as events that may compromise the pristine structure occur and remain unrepaired.

Thus, what is needed is an onboard Structural Health Monitoring (SHM) system enabled to perform maintenance inspections with a high probability of detection without requiring physical or visual access to the components, thereby decreasing the cost of maintenance on current and future air vehicles.

SUMMARY

The present disclosure endeavors to provide an SHM process using electrically conductive layers (e.g., carbon nanotubes (CNT, also known as buckytubes), copper, etc.) to measure changes in a layered structure. Electrically conductive layers may be embedded in the outer layers of a layered component using known manufacturing processes, for example, hand lay-up. CNT layers enable the layered structure to act akin to a capacitor that may be measured using known practices. For example, it is possible to measure the change in capacitance of a material over time to detect changes to the material or material systems (e.g., measuring the rise time of a signal on the formed capacitor when a voltage is applied to the sensor layers).

According to a first aspect of the present invention, a method for detecting a change in the structural integrity of a layered structural component includes the steps of: providing a layered structural component having embedded conductive layers on at least two substantially parallel surfaces of the layered structural component, wherein the conductive layers are electrically insulated from the layered structural component; then measuring an electrical capacitance by detecting changes in the dielectric of the material between the conductive layer. The measured electrical capacitance is then compared to a reference value; the deviation from the reference value indicates a change in the structural integrity of the layered structural component.

According to a second aspect of the present invention, a system for detecting a change in structural integrity of a layered structural component includes two conductive layers embedded on at least two substantially parallel surfaces of a layered structural component. The conductive layers are electrically insulated from the layered structural component. A device is provided for detecting changes in the dielectric of the material between the conductive layers, to measure an electrical capacitance. A monitoring device is also provided, for comparing the measured electrical capacitance to a reference value. The deviation from the reference value indicates a change in the structural integrity of the layered structural component.

According to a third aspect of the present invention, a system for detecting a change in the structural integrity of a structural component comprises: a conductive layer sheet located on at least one surface of a structural component, wherein said conductive layer sheet is electrically isolated from the structural component and comprises at least one conductive layer; a device for detecting changes in the dielectric of the material between said at least one conductive layer and a second conductive layer to measure an electrical capacitance; and a monitoring device for comparing the measured electrical capacitance to a reference value, wherein deviation from the reference value indicates a change in the structural integrity of said layered structural component.

According to a fourth aspect of the present invention, a method for detecting a change in the structural integrity of a structural component comprises the steps of: placing conductive layers on two opposite surfaces a structural component, wherein said conductive layers are electrically isolated from the structural component; detecting changes in the dielectric of the component between said conductive layers by measuring an electrical capacitance between the conductive layers; and comparing the measured electrical capacitance to a reference value, wherein deviation from the reference value indicates a change in the structural integrity of said layered structural component.

In certain aspects of the present invention, the conductive layers may contain: (i) carbon nanotubes; (ii) metallic material; (iii) metal mesh; (iv) metalized bondable polymer films; (v) non-metallic electrically conductive material; and (vi) combinations thereof.

In another aspect of the present invention, the conductive layers may be insulated from the layered structural component using a bondable polymer film insulation.

In another aspect of the present invention, the conductive layers may cover the total surface of the layered structural component or a portion thereof.

In yet another aspect of the present invention, the reference value represents a baseline capacitance measurement, wherein the baseline capacitance measurement for a layered structural component may be determined after the layered structural component's fabrication but prior to substantial use of the layered structural component. The measured baseline capacitance may be used as a reference point to detect changes in the component's structural properties. Alternatively, a measured baseline capacitance measurement may be compared to the capacitance measurement of a reference layered structural component, to detect manufacturing defects and/or used as accept or reject criteria for manufactured parts.

In yet another aspect of the present invention, each conductive layer comprises multiple strips of conductive material, wherein the strips of conductive material on the at least two surfaces of the layered structural component may not be parallel, resulting in a grid of strips to allow localization of damage to regions where strips overlap.

In yet another aspect of the present invention, one or more conductive panels cover an area of a first side of the layered structural component and two or more, smaller conductive panels are used to cover the other side of the same area thereby allowing localization of damage within the area of the smaller damaged conductive panels.

In yet another aspect of the present invention, the capacitance may be measured by applying a signal waveform to a conductive layer and measuring a parameter of the layered structural component.

In yet another aspect of the present invention, the width of the conductive strips may be varied to adjust the resolution of a detectable change in the structural integrity of the layered structural component. Similarly, the area of the smaller conductive panel may be varied to adjust the resolution of a detectable change in the structural integrity of the layered structural component.

BRIEF DESCRIPTION OF THE DRAWINGS

These and other advantages of the present invention will be readily understood with reference to the following specifications and attached drawings wherein:

FIG. 2 is a graph illustrating residual strength ($\sigma$) over the lifetime design (t) space;

FIGS. 4a through 4c are top plan views illustrating various exemplary configurations of CNT strips and panels;

DETAILED DESCRIPTION

Figure 1:
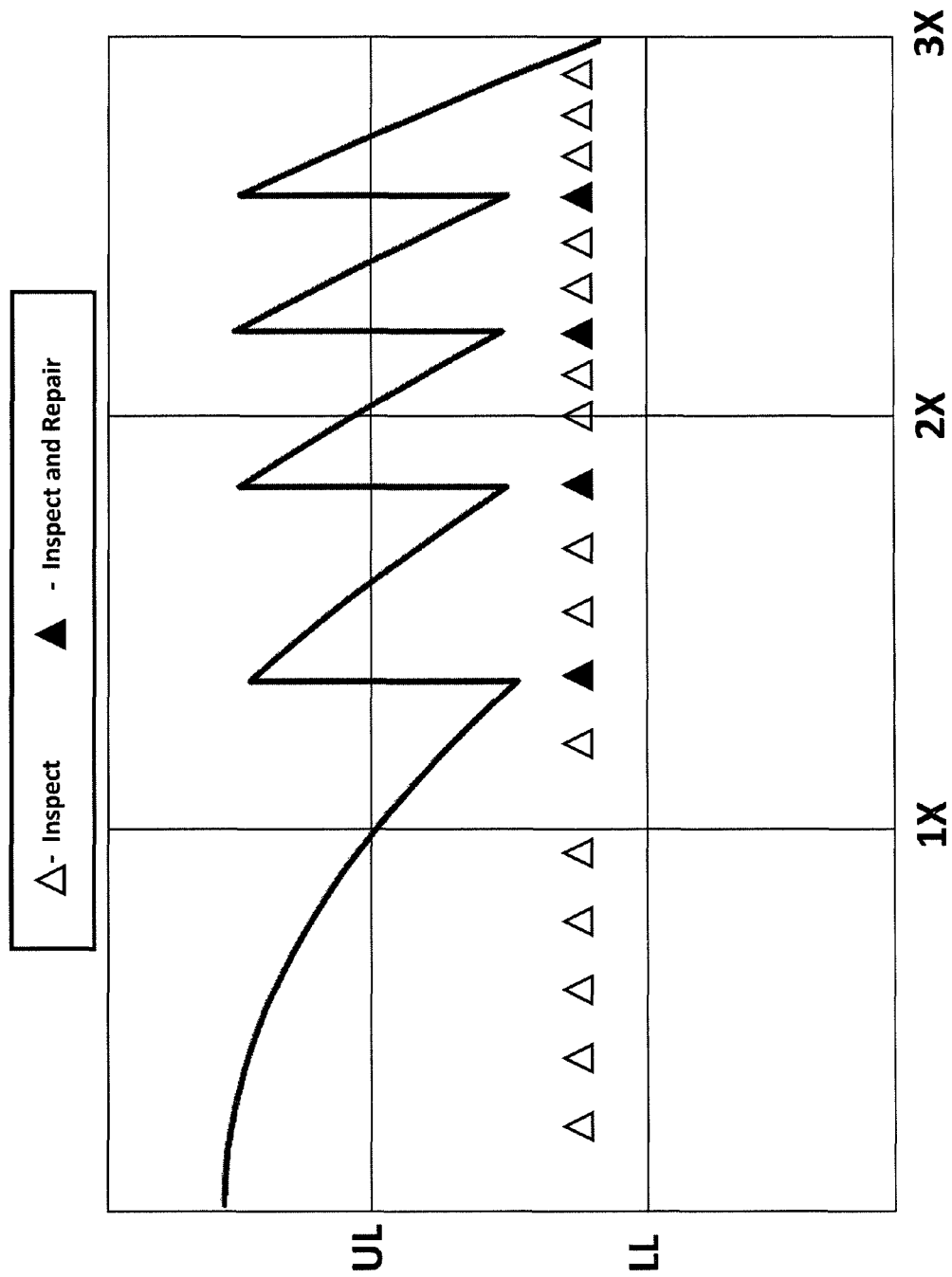
FIG. 1 is a graph illustrating a typical inspection and repair schedule over the life of the Air Vehicle.

The present disclosure endeavors to provide an SHM system and method, preferably using CNTs, to measure structural changes in a layered structure. A preferred embodiment of the present invention will be described hereinbelow with reference to the accompanying drawings. In the following description, well-known functions or constructions are not described in detail since they would obscure the invention in unnecessary detail.

Reducing the man-hours required to conduct inspection and performance assessment of structural components may be accomplished in at least one of two ways: (i) by making structural components more accessible or (ii) by utilizing technologies that enable remote inspection. The former option, designed for manual inspection and accessibility, creates conflicting design constraints in both manufacturing and weight budgets. Access and inspection points are undesirable because they increase the number of parts within an aircraft's structure while adding weight and complexity to the structure. Complexity itself often adds the need for additional maintenance while increasing manufacturing costs. Fortunately, the second option, structural health monitoring, allows for remote damage detection. Remote inspection obviates the need for component access for inspection purposes and saves the direct maintenance man-hours associated with those inspections.

Remote damage detection may be accomplished using, for example, a capacitance-based SHM system embedded within a vehicle's (e.g., aircraft, watercraft, land craft and any other vehicle where monitoring the integrity of a structure would be desirable) layered structure. For instance, when applied to an aircraft, a capacitance-based SHM system could provide aircraft maintenance crews with the ability to inspect and evaluate the structural integrity of the airframe components in a cost-efficient manner, because a scan of the aircraft could be completed almost instantaneously. A capacitance-based SHM system removes the need for a maintenance technician to manually scan the structure, a process that is normally done by passing a hand-held sensor over the structure. Since a scan using a capacitance-based SHM system may be automated, human variability in scanning can also eliminated. Additionally, reducing the need for access points simplifies the structure and reduces its overall weight. Finally, the completed scans serve as a recorded history of the aircraft's structure, allowing maintenance technicians to monitor the residual strength of the structure. The results from the scans or SHM system may be delivered to one or more remote third parties (e.g., aircraft maintenance personnel) or reported directly to the pilot to warn of damage to the aircraft during flight so that the pilot can respond accordingly (e.g., land, slow down, etc.).

The ability to use an SHM system for damage detection in layered components allows for a reduction in the amount of traditional NDE that must be performed at intervals on an aircraft. An SHM system also increases the scope of components that may be inspected without requiring the removal of panels to virtually all components and areas of the aircraft. Presently, inspection areas are limited by the airframe weight and cost budgets due to weight and cost of the sensors. A capacitance-based SHM system, as compared to more traditional NDE methods, reduces time-consuming and costly NDE setups with a robust and lightweight onboard SHM system. The SHM system performs equivalently to traditional NDE in accessible areas, while also granting inaccessible areas the same robust sensing capabilities without requiring the removal of panels or other components.

FIG. 1 is a graph illustrating a typical inspection and repair schedule over the life span of an aerial vehicle. An onboard SHM system can reduce the number of manual inspections required to ensure safe flight by moving from a scheduled inspection and maintenance system (hollow triangles) to a condition-based maintenance system (solid triangles) using the structural health readings generated by a capacitance-based SHM system (e.g., measured residual strength of the air vehicle), represented by a line. In the graph, UL represents the Ultimate Load and LL represents Limit Load where Limit Load is typically the maximum load anticipated to be carried by the structure under normal circumstances. Ultimate Load, on the otherhand, is typically equally to the Limit Load multiplied by a safety factor. For example, the safety factor for an aircraft may be 1.5. SHM sensors integrated into layered panels throughout the airframe will reduce maintenance hours associated with inspection for fatigue and damage throughout the aircraft by quickly detecting and localizing degradation. A remote data collection system may process the airframe health status, comparing it to previous flights and inspection points to determine the type and location of changes. Additionally, the data provided by SHM system may be compared to datasets of known flaws and damage and cross-referenced to the structural analysis of the airframe, which can ultimately be used to determine the type of damage, severity of damage, and residual strength of the component. This capability enables high-efficiency prognostic maintenance and reductions in system downtime.

Integration of SHM sensors with aerial vehicles allows for a valuable shift in the design of air vehicles. First, the use of an SHM system decreases the need for components and assemblies to be designed with access points to facilitate inspections throughout the airframe, making access points necessary only in areas requiring routine maintenance. Second, to curtail maintenance requirements, remote sensing functionality allows areas that are inaccessible to inspection to be designed to not need routine replacement without manual inspection. By utilizing remote inspections, an airframe designer may create unitized structures that are more lightweight, less costly, and more quickly assembled, reducing the number of access panels and accessibility features currently required to inspect the air vehicle.

FIG. 2 is a graph illustrating residual strength ($\sigma$) over the vehicle lifetime (t) where $\sigma$ represents a unit of stress (e.g., MPa, psi, etc.). The flight envelope available to a conventionally designed vehicle is limited to the rectangular space in the lower left-hand corner. However, regions A and B would be available to a vehicle enabled to tailor its flight to its residual strength using an SHM system. For example, a vehicle that is exposed to high stress levels will typically have a shorter life span (e.g., safe to fly while in region A). However, if a vehicle does not accumulate a significant amount of damage over its designed lifetime (the time prior to the design point), the vehicle may operate for a greater amount of time, thereby extending its life into region B.

To provide sensor functionality, CNT material (e.g., CNT sheets, ribbons, strip, or combinations thereof) or another conductor material are preferably embedded into the outer layers of a layered component using standard manufacturing processes, for example, hand lay-up. Inserting electrically conductive layers enables the structure to function similarly to a capacitor that is measurable using common practices. Generally speaking, a capacitor device is a passive electronic component comprising a pair of conductors (e.g., CNT layers) separated by a dielectric (e.g., structural layers and/or core). When there is a potential difference (voltage) across the conductors, a static electric field develops across the dielectric, causing positive charge to collect on one plate and negative charge on the other plate. Energy may be stored in the electrostatic field. For example, the rise time of a signal on the capacitor-like structure formed using CNT in an SHM system may be measured when a voltage is applied to the sensor layers. While the description centers on use of CNT conductors, it is clear to those of skill in the art that other conductive materials may be employed, including, for example, metallic materials, non-metallic conductive materials, or any other material capable of conducting electricity. Metallic materials may include, for example, metals (e.g., aluminum, copper, silver, gold, etc.) and metal alloys. Non-metallic conductive materials may include, for example, graphite and other carbon based materials. In certain embodiments, a conductive material may be woven or embedded with a non-conductive material to yield a hybrid material that may be used as an electrical conductor.

In another aspect, conductive layers may be applied to an existing structure in a secondary operation to enable retrofitting of existing vehicles with SHM technology. This would be particularly useful in instances where additional SHM functionality is desirable but was previously unavailable. For example, conductive layer sheets may be manufactured as a combination of, for example, conductors, insulating film layers, and film adhesive and delivered in a sheet form ready to be applied onto each side of a composite structure where each sheet acts as a capacitor plate to create a capacitance system. Similarly, according to another aspect, a single sheet may be manufactured comprising two or more conductive layers separated by a dielectric wherein the sheet need only be applied to a single side of a structure (e.g., the surface to be monitored). While this type of sheet may not be able to readily detect the vehicle component's internal structural fatigue or internal damage, it would be able to easily detect surface damage (e.g., structural fatigue caused by FOD) and may be enabled for installation on a traditional metallic structure, provided that the electrical conductors are isolated from the metallic surface.

Numerous suitable devices, meters, and methods are available for measuring capacitance and may be used with the CNT SHM system. For example, a Schering Bridge, a type of bridge circuit, may be used to determine an unknown electrical capacitance and its dissipation factor in dielectrics. The dissipation factor of a capacitor is the ratio of its resistance to its capacitive reactance. Generally speaking, the Schering Bridge is basically a four-arm alternating-current (AC) bridge circuit whose measurement depends on balancing the loads on its arms. For further information on measuring capacitance, see, for example, "AC Bridges: Measuring Capacitance using de Sauty and Schering Bridges" by Ravitej Uppu, available at http://www.cmi.ac.in/~ravitej/lab/acbrid-capacitance pdf.

As mentioned, the outer layers of the laminate may comprise one or more CNT layers separated from the structural laminate by a polymer barrier to form a capacitor-like structure that causes the material (e.g., structural layers and/or core) between the CNT layers to act as the dielectric medium. In essence, the structural component (e.g., material between the CNT layers) may generally be a dielectric medium that may be affected by damage and liquid intrusion and will thus detect and measure this damage.

The varying differences in the dielectric constants of various materials act as a basis for the system's ability to detect damage to the structure. For instance, if a core material is saturated with a liquid (e.g., from a leak or crack), there should be a significant change in capacitance due to the large difference between the dielectric constants of air and other material (e.g., water, graphite, liquids, etc.). Since the dielectric constant of air is 1.0 at Standard Temperature and Pressure (STP) and the dielectric constant of water is approximately 80 at 20° C., a capacitor with water between the conductive layers will have capacitance 80 times greater than an air capacitor, due to the difference in the dielectric constant of the two materials. Because capacitance is generally deterministic, capacitance measurement is the preferred measurement method, but other methods may be used; for example, the resistance of CNT strands may be monitored for damage.

Over the last decade, CNTs have become an increasingly viable material for both structural and electrical uses. Carbon nanotubes, not to be confused with carbon fiber, are allotropes of carbon with a cylindrical nanostructure and are an ideal conductor for embedded signal application. Another suitable conductor may be carbon nanofibers/nanofilaments (CNF). CNFs (aka vapor grown carbon fibers (VGCF) or vapor grown carbon nanofibers (VGCNF)) are nanostructures with graphene layers arranged as stacked cones, cups, or plates, whereas CNTs are carbon nanofibers with graphene layers wrapped into cylinders. CNTs and other carbon-based materials may be used to construct an onboard embedded system for monitoring the health of various layered aircraft surfaces without necessitating the need to remove body panels to physically inspect a surface.

CNTs and CNFs are, generally speaking, superior materials for embedment than other, more traditional, materials such as copper. First of all, copper has a higher coefficient of thermal expansion (CTE) than carbon (copper is ~16.6×10-6 m/m K while carbon is ~2×10-6 m/m K), which causes a change in volume in response to a change in temperature, lower strength, and a higher modulus that inhibits its flexibility. Secondly, copper is also prone to strain hardening which can cause the material to become brittle over time. These factors combine to make copper highly susceptible to breakage and damage as an embedded conductor. Conversely, CNFs and CNTs' CTE, lower modulus, similarity to carbon fiber (e.g., they are part of the same family), and high strength have the exact opposite effect, combining to handle large temperature swings and vibration, while flexing with the structure. For these reasons, CNT and CNF materials are superior to copper for embedment applications. In addition, CNTs and CNFs can be folded and bent onto themselves without breakage, allowing them to be routed in the sharp corners and curves of layered structures. This property and their high strength enables CNF and CNT harnesses to have tight bend radii when exiting connectors.

This CNT and SHM technology may be applied to any combination of materials, including, but not limited to, honeycomb core, foam core, glass, carbon fiber, and epoxy. Any change in the capacitance properties would indicate a change in the aircraft's structure, and the amount of capacitance change can be correlated to the type and extent of the structural damage. For example, in addition to an event such as water intrusion, micromechanical failures can be detected. Cracks in the matrix material, delamination, and fiber breakage would cause a change to the dielectric constant that the structure possesses. The resolution of an SHM system can be determined based on the desired minimum flaw tolerance to be detected when compared to standard data points.

Figure 3A:
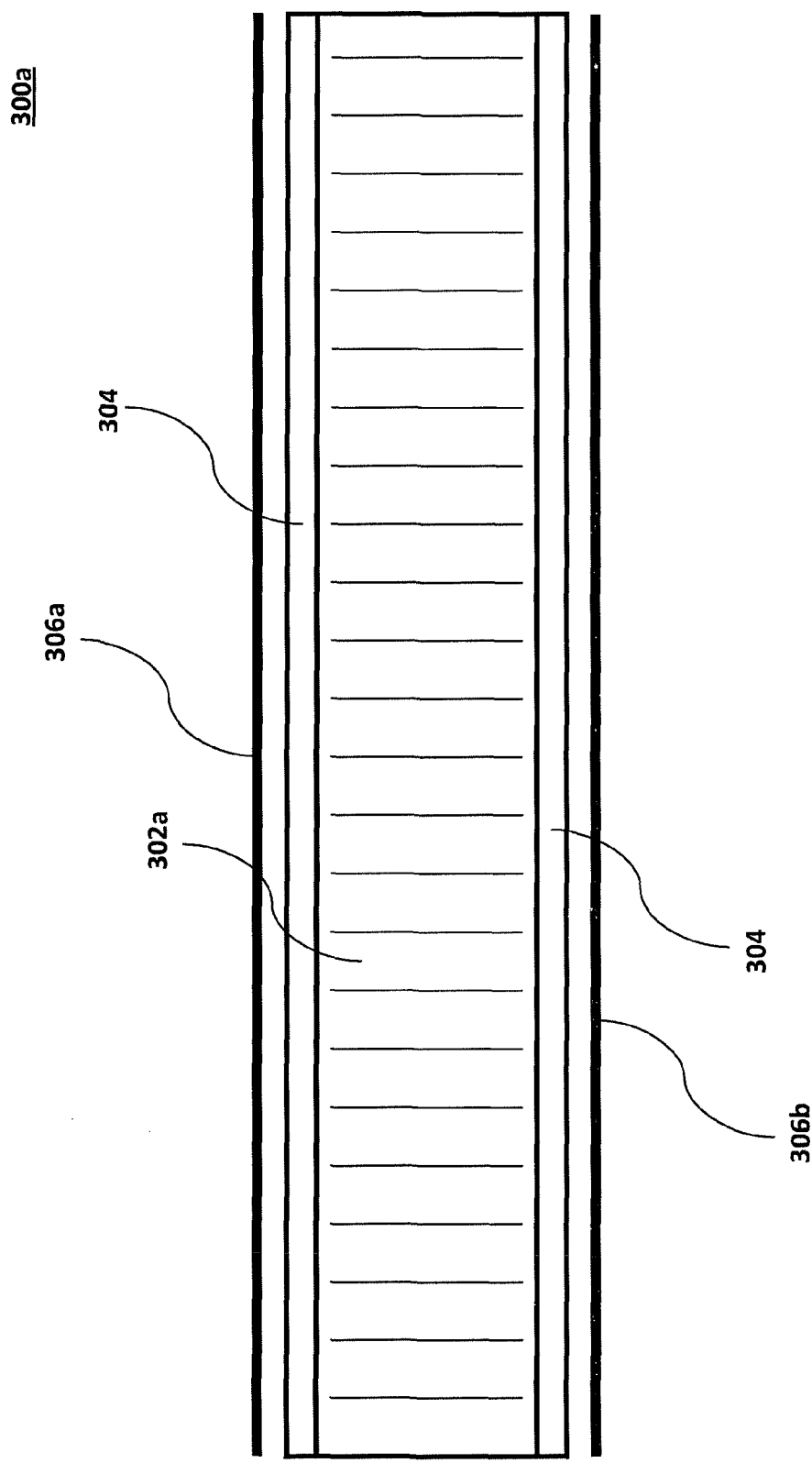
FIGS. 3a and 3b are cutaway side views illustrating an exemplary configuration of sensor layers.
Figure 3B:
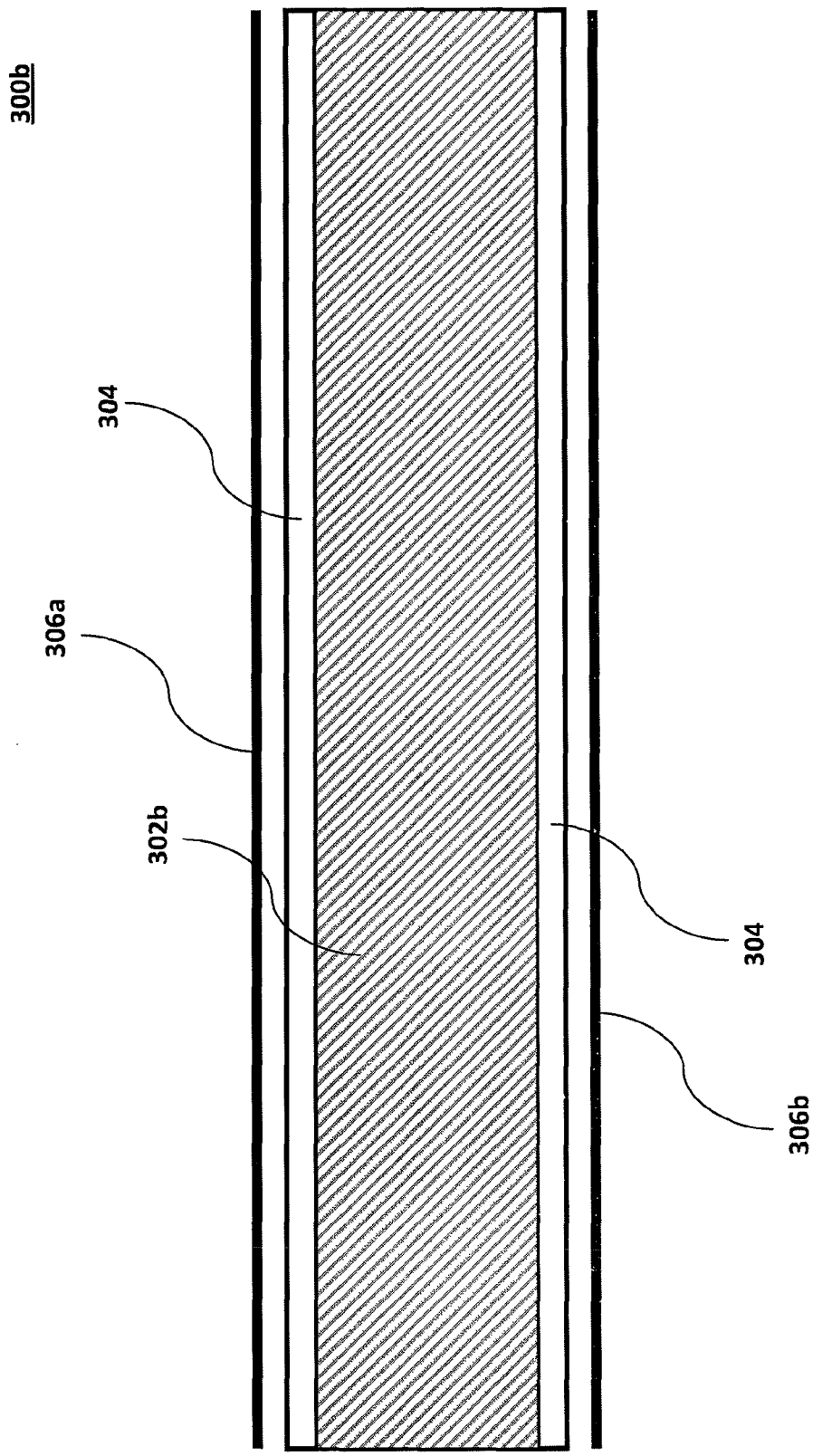

FIG. 3a is a cutaway side view illustrating a first configuration 300a of a capacitor-based sensor layer. The structure 300a generally comprises one or more structural layered layers 304, a honeycomb/foam core 302a, and CNT layers 306 (e.g., a first layer 306a and a second layer 306b). In FIG. 3a, the honeycomb/foam core 302a and structural layers 304 would function as the capacitor's dielectric and the first and second CNT layers 306a, 306b would function as the capacitor's plates. While only a single layered layer 304 is shown on each side of the honeycomb/foam core 302a, one having ordinary skill in the art would appreciate that multiple layers may be installed on each side of the honeycomb/foam core 302a. Similarly, FIG. 3b is a cutaway side view illustrating a second configuration 300b of the sensor layers. As in FIG. 3a, the structure 300b generally comprises one or more structural layered layers 304, and one or more CNT layers 306a and 306b. However, rather than a honeycomb/foam core, the core 302b may be a another material (e.g., glass, carbon fiber, and/or resin).

Capacitance measurement is preferable over resistance as an SHM measurement because capacitance is inherently deterministic whereas resistance depends on a current pathway. This can be problematic for resistance measurement because damage can affect the current pathway but it may not affect the resistance if other conductive pathways parallel to the damaged portion (this is akin to measuring resistance on a printed circuit board with non-linear parts attached). However, the capacitance measurement is based on the field between the two plates, the fringe effects of the plates, and the dielectric property of the material between the plates. Variations in this field are based only on changes within the dielectric medium and the distance between the capacitive layers. Thus, changes are inherently deterministic in respect to damage and changes to the dielectric medium. Moreover, using capacitance may be preferred as it is path independent. For example, if the scans were to measure resistance of the structure, a change in the structure would also change the path of the circuit being used to measure the resistance. Therefore, the structure could be damaged, but because the path for the current can also altered, there may not be a measurable change to the resistance of the structure due to the damage.

The equation for capacitance is shown below where $\varepsilon_r$ is the dielectric constant of the material between the sensor layers, $\varepsilon_0$ is the electric constant, A is the area of the capacitive layers, and d is the distance between the capacitive layers (i.e., the thickness of the structural laminate).

$$C = \varepsilon_r \varepsilon_0 \frac{A}{d} \qquad \text{Equation 1}$$

Each laminate may have a dielectric constant, $\varepsilon_r$, based on its thickness and the materials that make up the laminate (e.g., carbon fiber, epoxy, and core). The alterations to the structural laminate will cause changes to the structure's dielectric constant. Changes may include, but are not limited to, damage caused by matrix cracking, impacts, delaminations, void growth and liquid intrusion. Impact damage that causes an indentation in the laminate will be evident, as capacitance is inversely proportional to the distance between the sensor layers. Software to distinguish and determine the various types of damage and determine if a repair is needed may be implemented to further streamline the SHM system. For example, software may take a number of factors into consideration when determining the type or extent of damage by comparing current values to a reference value, such as, for example, a baseline capacitance value for a specific vehicle component. The factors may include, for example, location of the component, location of the damage (i.e., area of the component), and extent of the damage. To establish baseline capacitance values, a capacitance scan of the structure or component may be taken after the part has been manufactured. The capacitance scan of the same part may then be monitored over the life of the aircraft to determine what change in capacitance has occurred, indicating a change in the structure (i.e., change in integrity). For example, the scan may include a series of deltas (e.g., as a numerical value) to communicate the amount of structural change and/or capacitive fluctuation. The delta values may be visualized over a depiction of the component. In some aspects, the scan may further be colored coded based on the degree of deviance between an absolute value (e.g., actual value) and a reference value (e.g., a baseline capacitance value). For instance, areas with a lower delta value (e.g., less structural change) could be green and trend to yellow and then red as delta value increases (indicated that the degree of damage is increasing). Quantifying the amount of change relative to a type of damage can determine the amount of residual strength remaining in the structure (i.e., lifespan).

A capacitance-based SHM system may also be enabled to localize the damage within a structural component (i.e., to identify the location of the damage within a component). To achieve this, panels, or patches, of conductive material (e.g., CNT) are placed on opposite sides of the layered material or material system to be measured. Using this system, any defects or damage would be pinpointed between the affected panels. Similarly, one panel may be a grounded panel while the opposing panel may be a conductive material. Alternatively, conductive material may be formed into strips and laid across the surfaces of the structural component in two or more layers. The first layer of conductive material strips may be orthogonal to a second layer of strips, effectively forming a capacitive grid that can be sensed by taking a reading of a first layer strip versus a second layer strip. This configuration provides damage localization ability, in which localization resolution may depend on the signal-to-noise ratio (SNR) required to sense a minimum defect. This arrangement may also be used in resistance-based systems on the premise that a break in the surface would sever strips from each layer, thereby allowing the computer to use the X-Y coordinates to pinpoint the damaged area.

Figure 4C:
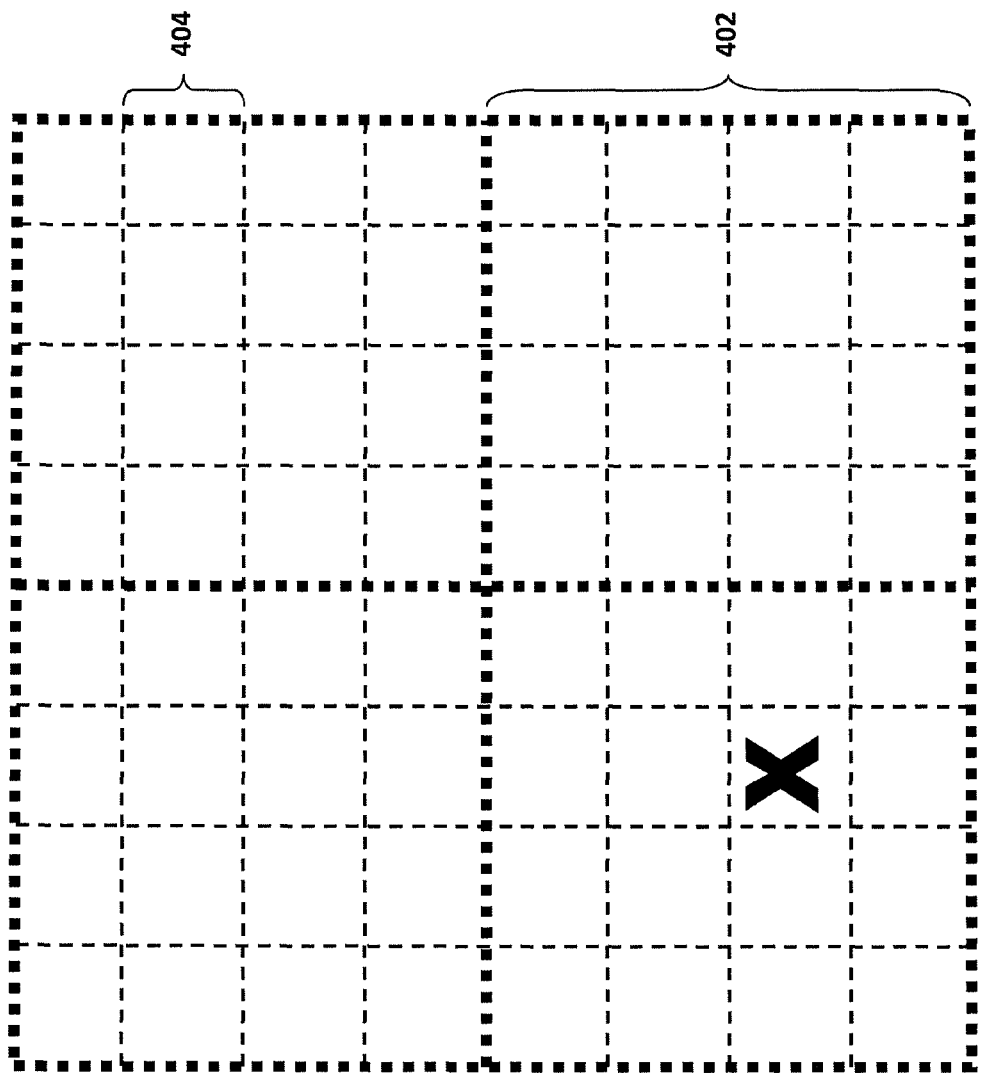

For example, FIG. 4a is a top plan view illustrating a first configuration of conductive material (e.g., CNT) strips. Arranging first and second layers of CNT strips to form a grid allows for a system to localize the damage within a structural component. By orienting the strips on one side of the laminate in one direction and the strips on the other side perpendicular to those, the strips form a grid. Each strip may be monitored, enabling the system to locate damage to or within an overlapping grid space. Similarly, FIG. 4b is a top plan view illustrating a second configuration of CNT strips. As in FIG. 4a, the first and second layers of CNT strips are arranged to form a grid allowing for a system to localize the damage within a structural component. However, the strips on one side of the laminate are not necessarily perpendicular to the strips on the other side but remain non-parallel to one another to form a grid. FIG. 4c illustrates a third configuration that may enable a system to localize the damage within a structural component. Contrary to FIGS. 4a and 4b, the configuration of FIG. 4c does not require strips but rather uses panels, or patches, to localize the damage. The first layer of conductors may include larger conductor panels 402, or areas, while the other layer would comprise smaller conductor panels 404, or areas, that may be used to pinpoint the area of the damage. The accuracy of the location would correlate to the size of the smaller conductor panel 404.

Therefore, varying the size of the strips (FIGS. 4a and 4b) or patches (FIG. 4c) can vary the sensitivity and resolution of both the locations and size of the defect. For example, if the smaller panel 404 of FIG. 4c is 2×2 inches, damage can be pinpointed to 4 square inches, while a panel of 12×12 inches would only permit damage pinpointing to 144 square inches. Naturally, the degree of desired accuracy would depend on the type and location of the component. For example, large visible areas such as external wing surfaces may be easier to examine thus less accuracy might be adequate whereas an internal component may require greater accuracy to limit the amount of deconstruction needed to located the damage.

The CNT material used to form the SHM system may be pre-impregnated with the same resin system as the structural plies prior to lamination. This allows the CNTs to act as a non-structural layer within the laminate without causing degradation to the structural laminate. As the sensors are built into the laminate during the component's cure process, it is possible to use the system as an acceptance criteria test, eliminating the need to do a detailed NDE examination of the newly fabricated component. For example, once a component has been fabricated, rather than manually inspecting it, the capacitance of the newly fabricated component may be measured and compared to stored capacitance values that correspond to acceptable components (e.g., reference value, baseline capacitance, etc.). While an SHM system may be embedded with or within a layered component material such that the SHM system is effectively part of the layered component, the SHM system may also be external to the layered component material such that the SHM system is a separate device used to measure the capacitance of a component.

Figure 8A:
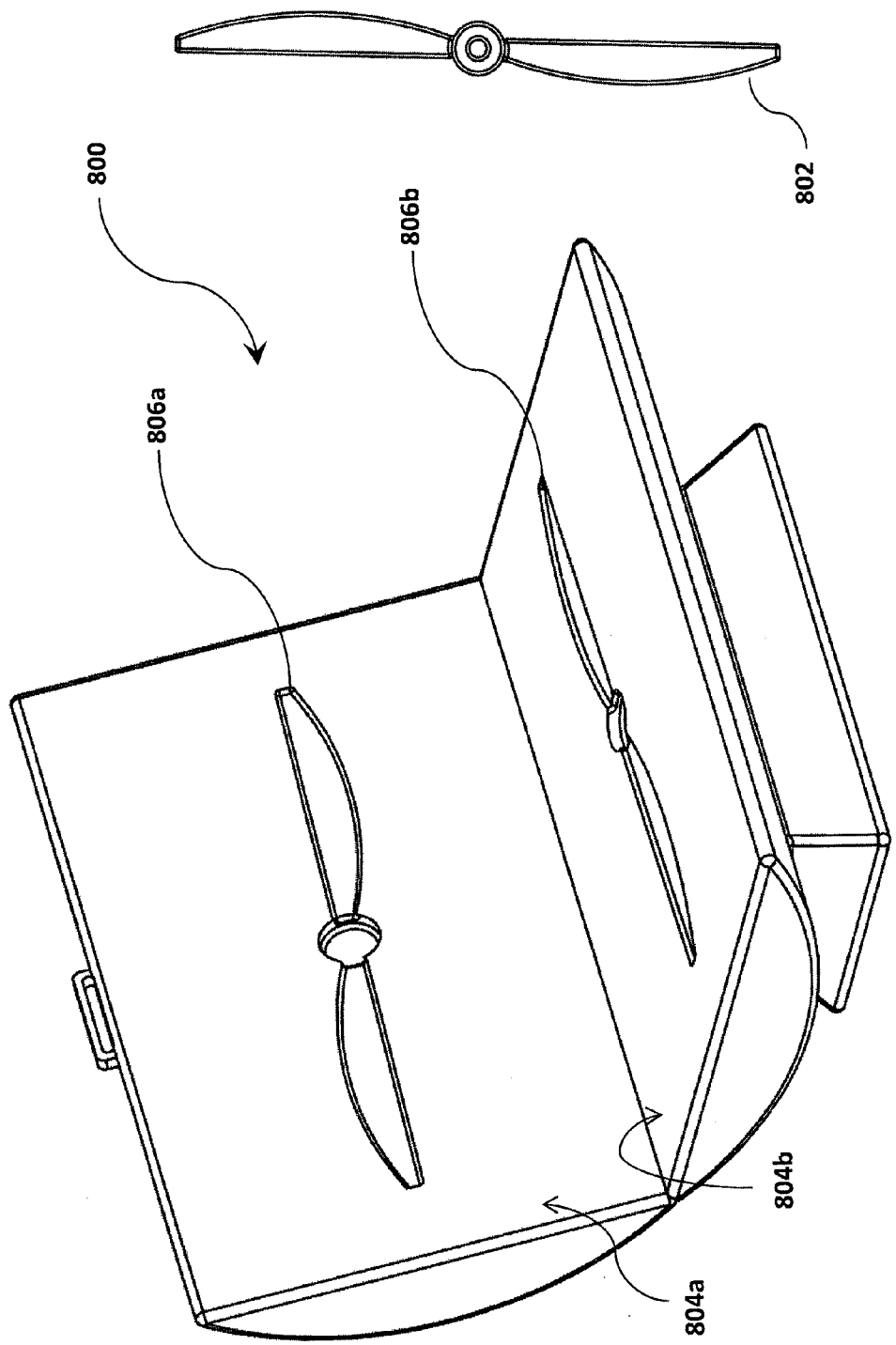
FIGS. 8a through 8c illustrate an exemplary capacitance scanning bed.
Figure 8B:
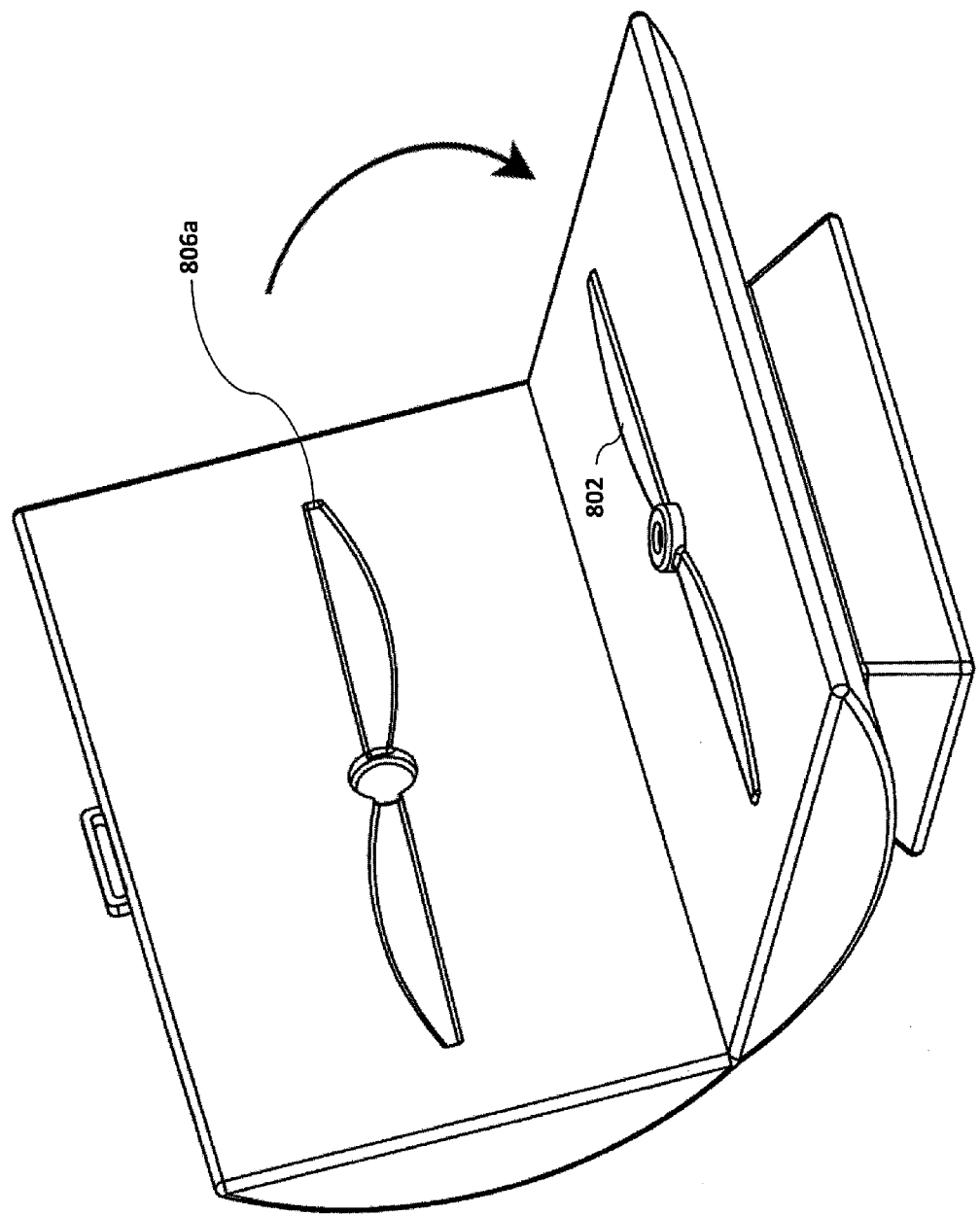
Figure 8C:
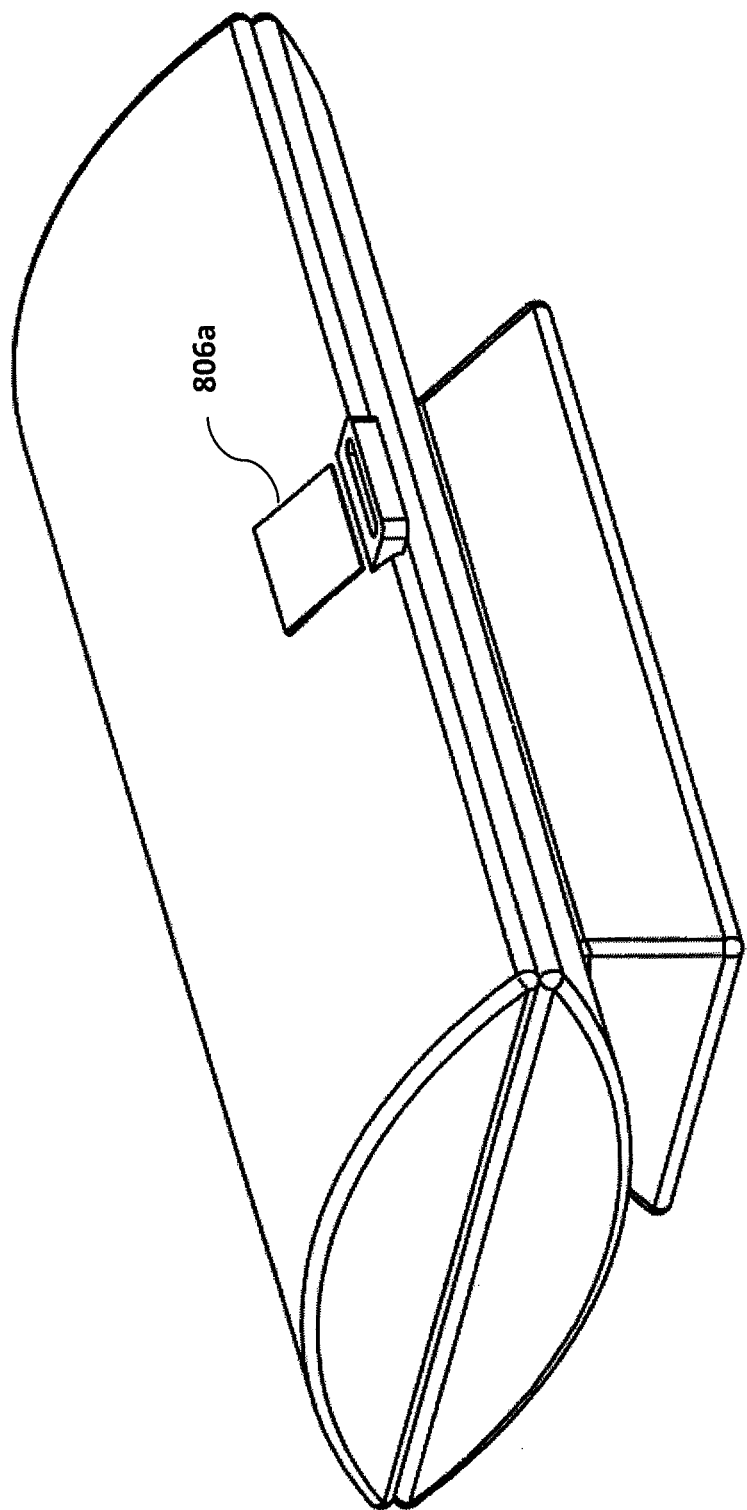

For instance, FIGS. 8a, 8b and 8c illustrate an exemplary capacitance scanning bed 800. A capacitance scanning bed 800 would be particularly beneficial for component quality control where embedded SHM functionality is unavailable. As with the embedded SHM system, a capacitance scanning bed 800 may be used as an acceptance criteria test. For example, once a component 802 (e.g., a propeller) has been fabricated, rather than manually inspecting it, the capacitance of the propeller 802 may be measured using the capacitance scanning bed 800 and compared to stored capacitance values that correspond to acceptable components (e.g., reference value, baseline capacitance, etc.). As illustrated in FIGS. 8a and 8b, the capacitance scanning bed 800 may comprise a hinged clam shell structure that surrounds the component 802. The inner surfaces 804a, 804b of the clam shells may be lined with sheets, or strips, of conductive material and configured to include recessed areas 806a, 806b designed to receive the component 802. The recessed areas 806a, 806b, which may be interchangeable allowing for different parts to be scanned using a single bed, may be customized for each component such that, when closed, the surface 804*a*, 804*b* of each clam shell half matches the contours of the component 802 being evaluated.

In other aspects, rather that using customized recessed areas 806*a*, 806*b*, each clam shell half 804*a*, 804*b* may be configured to automatically conform to the shape and/or contour of the component 802. For example, rather than using a rigid (or semi-rigid) material covered with conductive material, a plush material may be inserted into each half and covered with a conductive material layer. The plush material may be, for example, a polyurethane having additional chemicals that increase viscosity and density. This form of polyurethane is often referred to as "visco-elastic" polyurethane foam, low-resilience polyurethane foam (e.g., LRPu), or "Memory Foam." The ability to automatically conform to the shape and/or contour of the component 802 would eliminate the need to fabricated multiple recessed area cavities and/or capacitance scanning beds 800 thereby avoiding unnecessary costs and wasted time since a single capacitance scanning bed 800 could be used to evaluate multiple components 802 having diverse shapes and sizes.

The capacitance scanning bed 800 would employ capacitance measurement techniques similar to that of the embedded SHM system wherein each clamshell half's conductive layer would represent a capacitance plate while the component 802 functions as the dielectric. As with the embedded SHM system, any capacitance variation within the component 802 would indicate structural changes. To simplify measurement, the capacitance scanning bed 800 may further include a display 808 (e.g., an LCD display) enabled to display, for example, the measured capacitance value and/or a "PASS"/"FAIL" indicator. Similarly, the results of the capacitance scan may be communicated to, for example, a computer, monitoring station, or other third party.

Figure 9A:
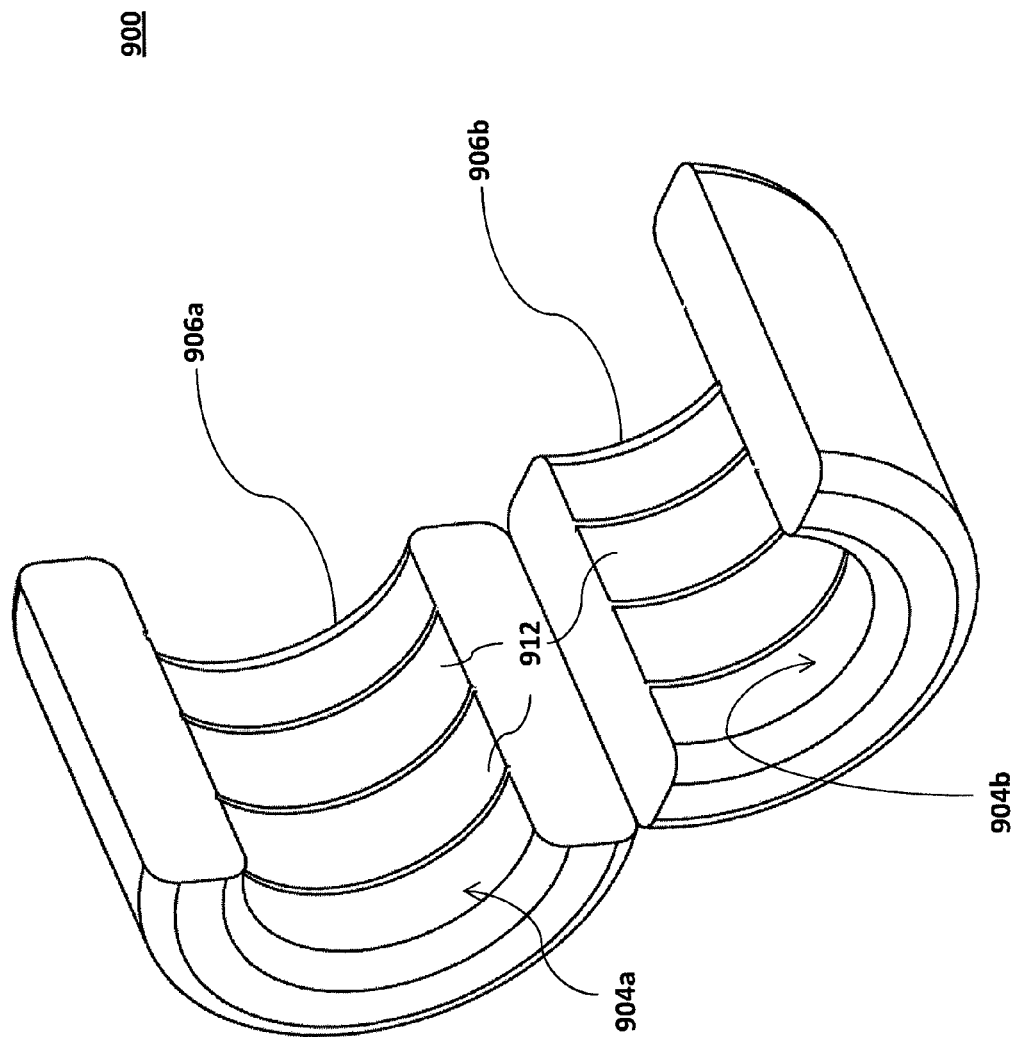
FIGS. 9a through 9d illustrate an exemplary movable capacitance scanner.
Figure 9B:
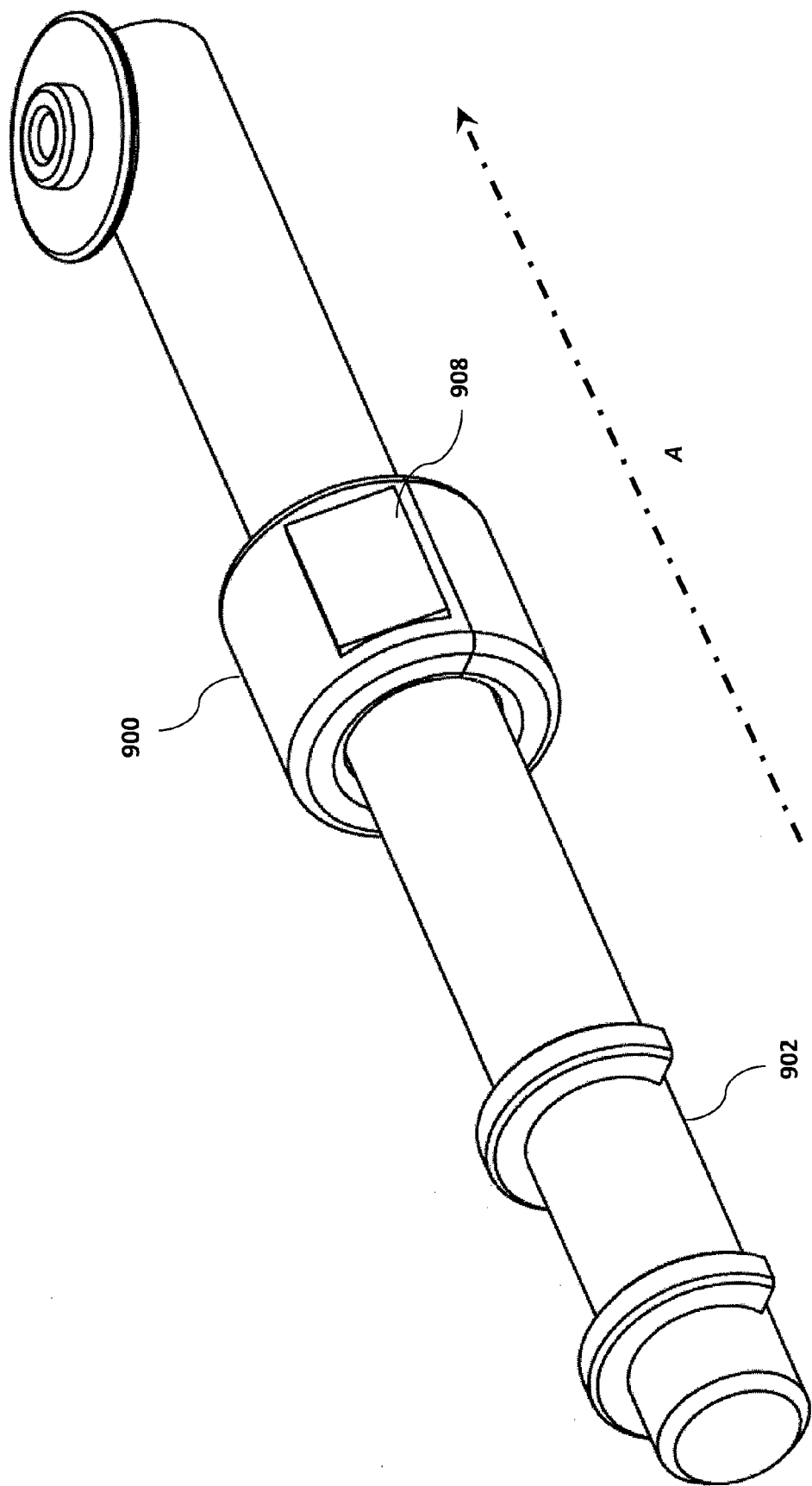
Figure 9C:
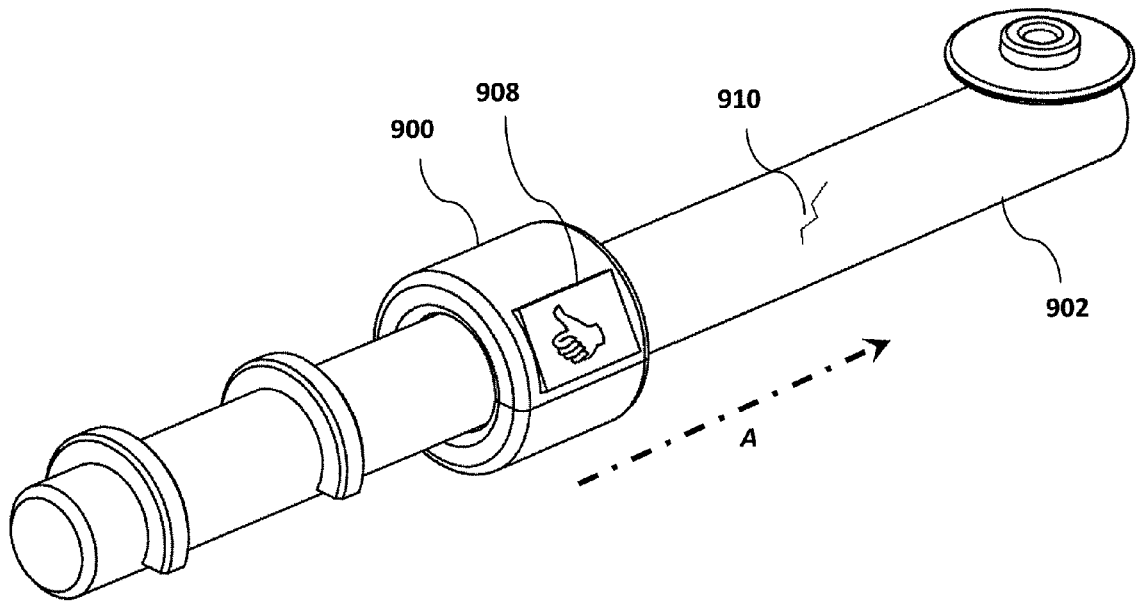
Figure 9D:
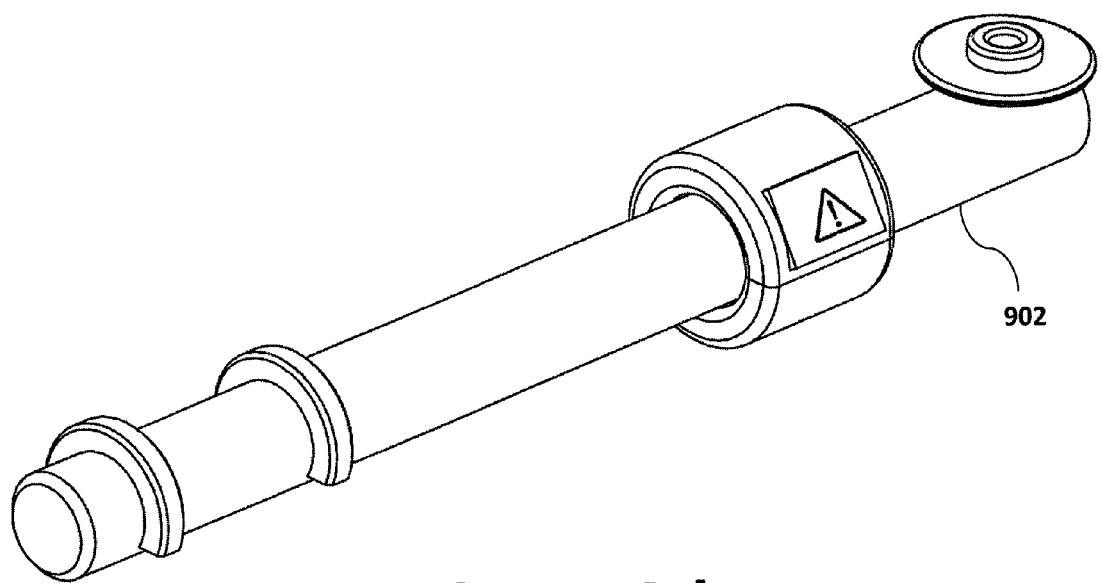

Referring now to FIGS. 9*a* through 9*d*, an exemplary movable capacitance scanner 900 is shown. In certain situations, it may be impractical or impossible to place a component onto a capacitance scan bed (e.g., wing struts), thus it would be advantageous to have a movable capacitance scanner. The movable capacitance scanner 900 may be described as a portable version of the capacitance scanning bed 800 of FIGS. 8*a* through 8*c* and maybe be independently functional (e.g., contains all necessary processors and electronics to be fully operable) or may be tethered (wired or wirelessly) to a capacitance scanning bed 800. As illustrated in FIG. 9*a*, the movable capacitance scanner 900 generally comprises two clam shell halves wherein each inner surface 904*a*, 904*b* of the clam shell may be lined with sheets, or strips, of conductive material 912. In operation, the movable capacitance scanner 900 may be closed around the component 902 and moved lengthwise A along the component 902. As the capacitance scanner 900 is moved, the capacitance of the component 902 is measured using techniques similar to those employed by the embedded SHM system. The capacitance value may then be displayed using display 908 or communicated to, for example, a computer, monitoring station, capacitance scanning bed or a third party. For example, referring now to FIGS. 9*c* and 9*d*, if the capacitance scanner 900 is passed over an area where there is damage 910 (as indicated by a particular capacitance reading), the capacitance scanner 900 may sound an alarm or display a visual indicator.

In embedded applications, using materials that are similar to the host materials (i.e., the layered component materials) reduces the risk of the CNT layers behaving differently than the structural laminate. This difference in behavior has been a large downside of prior attempts at creating embedded systems. The system disclosed herein mitigates this downside. In fact, the CNT layers may provide a structural benefit by increasing the strength and/or stiffness of the various components.

SHM sensing functionality, along with other health and usage monitoring systems, allows for complete monitoring of aircraft load and health states during operation without requiring physical inspection. Vehicles, with control systems linked to the continuous monitoring of external events and airframe residual strength, can tailor the flight environment of the aerial vehicle to match the current structural capability. Thus, aerial vehicles may be pushed harder while remaining undamaged and operated safely as the structure degrades (e.g., due to gradual deterioration or other damage). By creating a system that can feel and react, much like that of a human skin with a nervous system, an airframe can operate based on real-time events and aircraft condition rather than estimated design limits.

An onboard SHM system may be integrated into virtually any type of vehicle and calibrated based on the type of vehicle. For instance, SHM integration with an air vehicle may begin with the aerial vehicle being operated in a safe and controlled manner to provide accurate reference numbers. By first integrating capacitance-base SHM sensing functionality into test specimens, the system may be developed to perform with a superior degree of accuracy and reliability. Another step for testing onboard SHM integration may be to install the system on a test aircraft into a low-risk location (e.g., a main rotor pylon for a helicopter). The integration may be more successful where the SHM system does not require structural design changes, and it can be used to perform NDE of incipient damage to reduce the immediate cost of maintenance.

Currently a majority of the NDE systems focus on inspections through ultrasonic and acoustic emissions, respectively. These systems essentially pulse waves through a structure while listening for a return either in pitch-catch or pulse-echo mode. Unfortunately, this type of system requires a highly trained operator to interpret the results from the scans. Additionally, the focused NDE scans are labor intensive and time-consuming to complete. The capacitance system disclosed herein may be conducted remotely and very quickly, instantly scanning the structure. Receivers may then obtain and process data and determine the location of the areas requiring repair or increased monitoring. The receivers may be located near the structure itself or be remote.

Figure 5A:
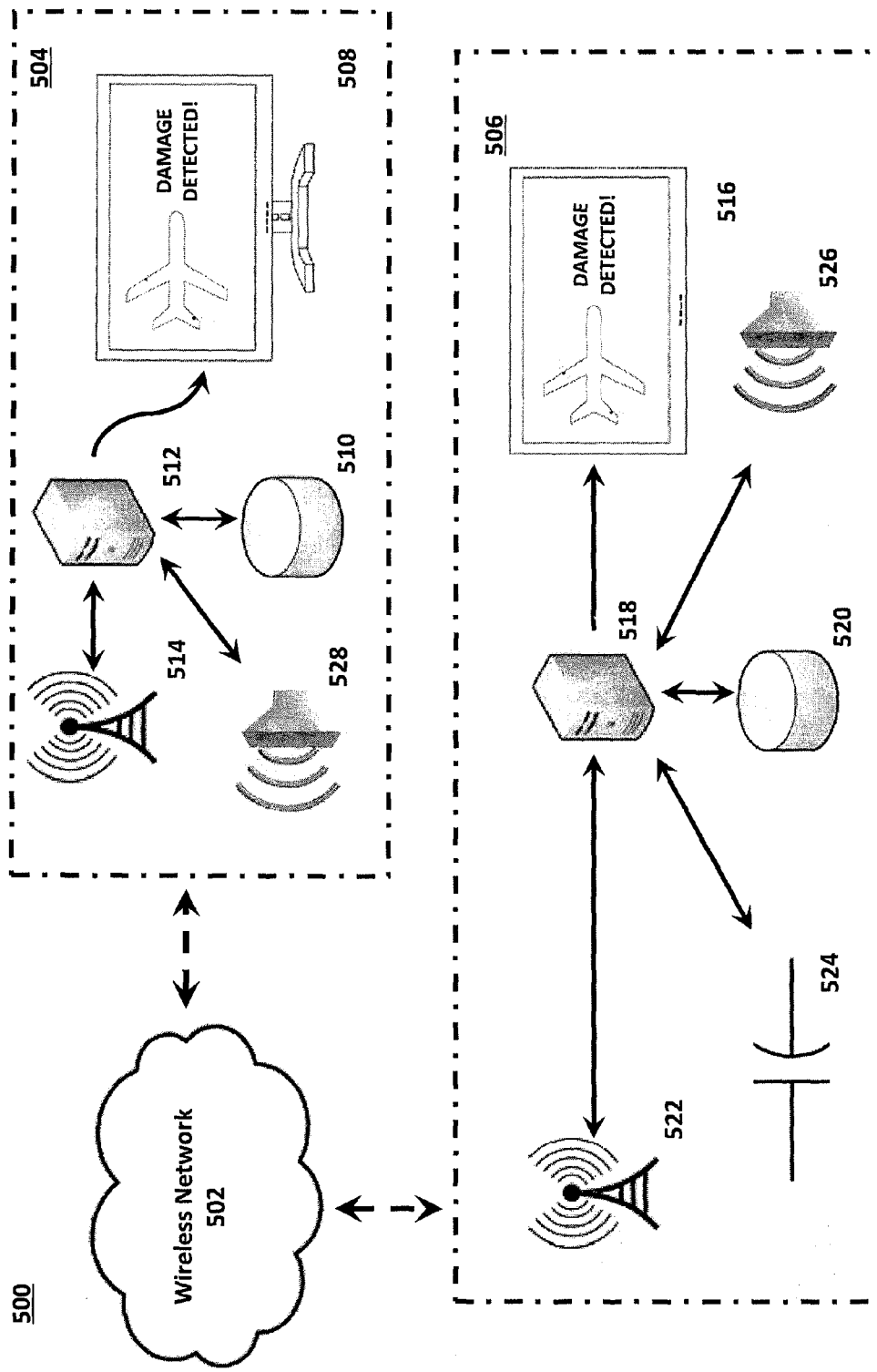
FIG. 5a is a diagram illustrating an exemplary system enabled to carry out SHM/NDE functionality.

FIG. 5*a* is a diagram illustrating an exemplary system enabled to carry out SHM/NDE functionality. The system may comprise a wireless network 502, an on-board monitoring system 506 and a remote monitoring system 504. The on-board monitoring system 506 could be integrated with an aircraft enabling the flight crew, or autopilot, to monitor the aircraft's structure and detect damage. The on-board monitoring system 506 may comprise a computer 518, storage device 520, visual display 516, speaker 526, wireless antenna 522 and one or more capacitance meters 524 to monitor the capacitance measure across the aircraft's various surfaces. The computer 518 could be any programmable device designed to sequentially and automatically carry out a sequence of arithmetic or logic operations. The computer 518 may be enabled to, for example, carry out calculations to determine if a capacitance value received from a capacitance meter 524 deviated from a particular range, thereby indicating a change in the aircraft structure (e.g., deterioration, damage, etc.). The computer 518 may be further enabled to log and store various measurements and values to the storage device 520. For example, the storage device 520 may be used to store the values collected over the life span of the aircraft to create a complete flight history that would include any changes to the aircraft structure. The one or more capacitance meters 524 may use any known capacitance measurement techniques including, for example, the Schering Bridge (illustrated in FIG. 5b). While the one or more capacitance meters 524 is illustrated as being separate from the computer 518, capacitance measuring functionality may be integrated with the computer 518 such that electrical leads may be used to simply connect the computer 518 directly to the capacitor device being measured or monitored (e.g., an aircraft panel).

The on-board monitoring system 506 may further comprise a visual display 516 and speaker 526 to alert flight crew of changes in the aircraft's structure. The visual display may be, for example, a traditional LCD display that could notify the user of any measured damage and the location of such measured damage. Similarly, an audible sound may be produced by the speaker 526 to alert the user of damage. The wireless antenna 522 may be used to relay the various gathered data and alerts to computers and/or personnel located outside of the aircraft.

For example, wireless antenna 522 may use the wireless network 502 to communicate data between the on-board monitoring system 506 and a remote monitoring system 504 via wireless antenna 522. The remote monitoring system 504 could be integrated with a flight control center or tower enabling the ground crew, or computer, to monitor an aircraft's structure and detect any changes in the structure. The remote monitoring system 504 may comprise a computer 512, storage device 510, visual display 508, speaker 528, and wireless antenna 514 to communicate the various data and alerts to computers and/or personnel located on-board the aircraft. The computer 512 could be any programmable device designed to sequentially and automatically carry out a sequence of arithmetic or logic operations. The computer 512 may be enabled to, for example, carry out calculations to determine if a capacitance value received, directly or indirectly, from an on-board capacitance meter 524 deviated from a particular range, thereby indicating a change in the aircraft structure (e.g., deterioration, damage, etc.). The computer 512 may be further enabled to log and store various measurements and values to storage device 510. For example, the storage device 510 may be used to store the values collected over the life span of the aircraft to creating a complete flight history that would include any changes to the aircraft structure.

As with the on-board monitoring system 506, the remote monitoring system 504 may further comprise a visual display 508 and speaker 528 for alerting ground crew of changes in the aircraft's structure. The visual display 508 may be, for example, a traditional LCD display that would notify the user of any measured damage and the location of such measured damage. Similarly, an audible sound may be produced by speaker 528 to alert the user of damage.

Figure 5B:
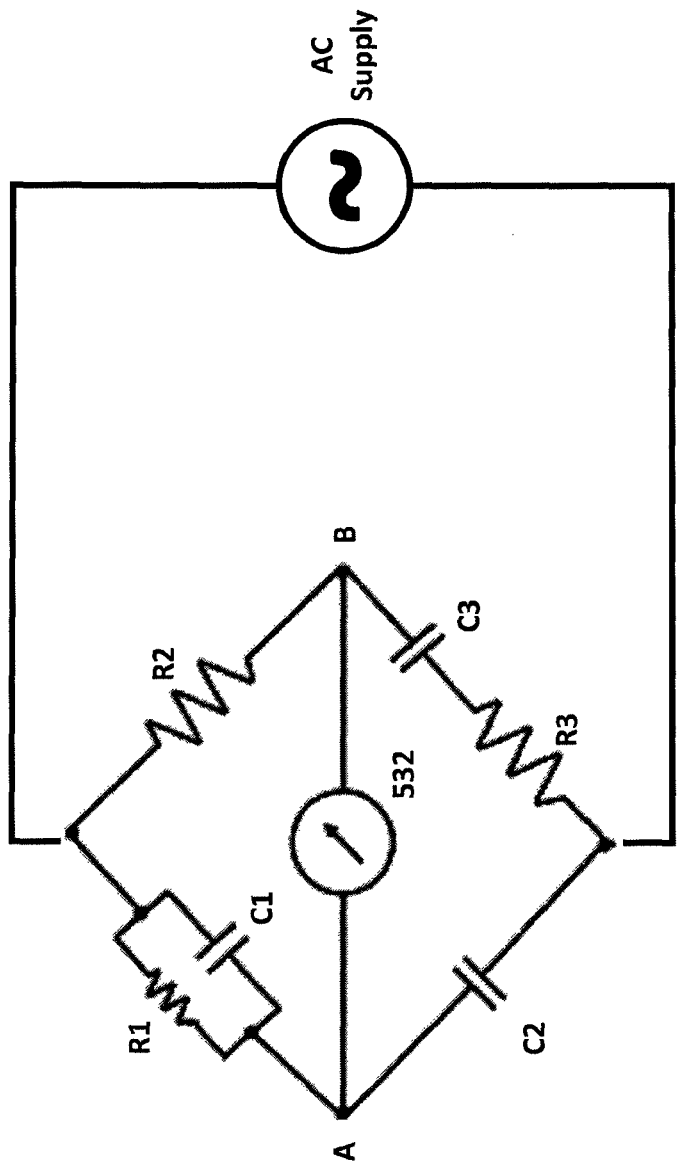
FIG. 5b is a circuit, known as a Schering Bridge, enabled for use in a system for carrying out SHM/NDE functionality.

FIG. 5b is a circuit, known as a Schering Bridge, enabled for use in a system for carrying out SHM/NDE functionality. In the Schering Bridge 530, the resistance values for resistors $R_1$ and $R_2$ are known, while the resistance value of resistor $R_3$ is unknown. The capacitance values of $C_1$ and $C_2$ are also known, while the capacitance of $C_3$ is the value being measured. To measure $R_3$ and $C_3$, the values of $C_2$ and $R_2$ are fixed, while the values of $R_1$ and $C_1$ are adjusted until the current through the ammeter 532 between points A and B becomes zero. This happens when the voltages at points A and B are equal, in which case the bridge is said to be balanced.

When the bridge is balanced, $Z_1/C_2 = R_2/Z_3$, where $Z_1$ is the impedance of $R_1$ in parallel with $C_1$ and $Z_3$ is the impedance of $R_3$ in series with $C_3$. In an AC circuit that has a capacitor, the capacitor contributes a capacitive reactance to the impedance. The capacitive reactance of a capacitor (C) is:

$$C = \frac{\pi \cdot f \cdot C}{2} \qquad \text{Equation 2}$$

When the bridge is balanced, the equation may be reduced to:

$$C_3 = \frac{R_1 C_2}{R_2} \qquad \text{Equation 3}$$

Figure 6:
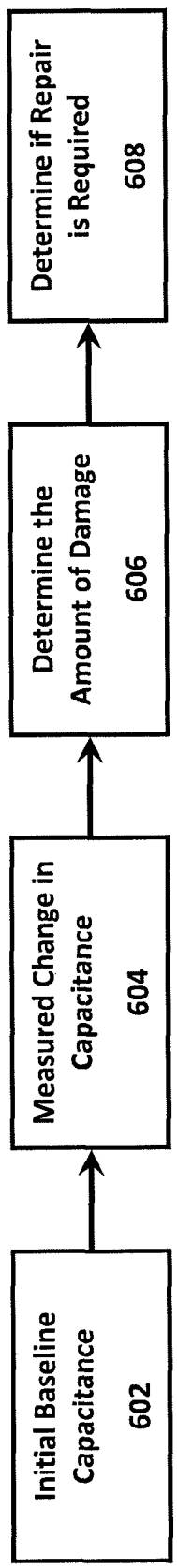
FIG. 6 is a flow diagram illustrating a processing of determining whether a repair is required using onboard SMH.

FIG. 6 is a flow diagram illustrating an exemplary process for determining whether a repair is required using onboard SHM. The system may measure the baseline capacitance of the component at step 602. To establish baseline capacitance values, a capacitance scan of the structure or component may be taken shortly after the part has been manufactured (e.g., post fabrication, but prior to use). The same capacitance scan of the part may then be monitored over the life of the aircraft at step 604 to determine what change in the capacitance, if any, has occurred. At step 606, the amount of change may be quantified relative to a type of damage to determine the amount of residual strength remaining in the structure (i.e., lifespan). This may be accomplished by comparing capacitance rise time to stored reference values to determine the degree of damage based on the difference between the two numbers. Based on the degree of damage and other factors (e.g., location of damage, type, component type, etc.), the SHM system may determine at step 608 whether to advise replacement or repair of one or more components.

To assess the accuracy of a capacitance-based SHM structural component and to verify a correlation between capacitance rise time and damage, a series of tests was performed on two different panels containing embedded CNT. The first panel was constructed from a solid laminate with a thickness of 0.175". The second panel was a honeycomb core panel with a total thickness of 0.46" and a core thickness of 0.375". In the test, holes with a diameter of 0.125" were drilled into each panel. Capacitance rise time was measured both before the holes were drilled and after each hole was completed. Results indicated that the capacitance rise time decreased with each additional hole, providing a clear correlation between damage and capacitance rise time (i.e., lower capacitance rise time indicated greater damage). See Table 1 below. In the test, capacitance layers were created using copper foil, because it provided the benefit of being extremely similar to the host material system, thereby reducing the risk of the system's affecting the laminate itself. However, other conductive layer materials may have been substituted for the copper foil, such as CNT material.

Prior to damage, the capacitance of the undamaged laminate was set as a baseline value. Incremental damage (e.g., additional holes or additional impacts) was then applied to the test panels. Measurements of the capacitance properties were taken and recorded. For these tests, damage was simulated by 0.125" diameter holes, drilled one at a time. The capacitance rise time was measured after each drilled hole. A summary of the capacitance rise times for each number of holes in the panels is shown below in Table 1. Copper strips were used in measuring the capacitance during preliminary testing. When used to pinpoint the location of the damage, strip widths may be chosen by the minimum detectable flaw desired. For example, when accuracy of the damage is crucial, narrower strips may be used to better pinpoint the location of the damage.

TABLE 1

Summary of Capacitance Rise Time Changes with Damage

| Number of 0.125" Holes | Solid Laminate Panel Rise Time (ns) | Honeycomb Core Panel Rise Time (ns) |
|---|---|---|
| 0 (Reference/Baseline) | 10.79 | 15.78 |
| 1 | 10.54 | 15.50 |
| 2 | 10.26 | 15.35 |
| 3 | 10.10 | 15.10 |
| 4 | Not Tested | 14.90 |

The tests revealed that the CNT-based SHM system disclosed herein successfully provides the ability to inspect and evaluate the structural integrity of airframe components using, for instance, an SHM system comprising capacitive sensors. The sensor system can be used to, for example, perform NDE, to remotely detect structural damage and/or monitor a layered airframe for small incipient damage in inaccessible areas.

Figure 7A:
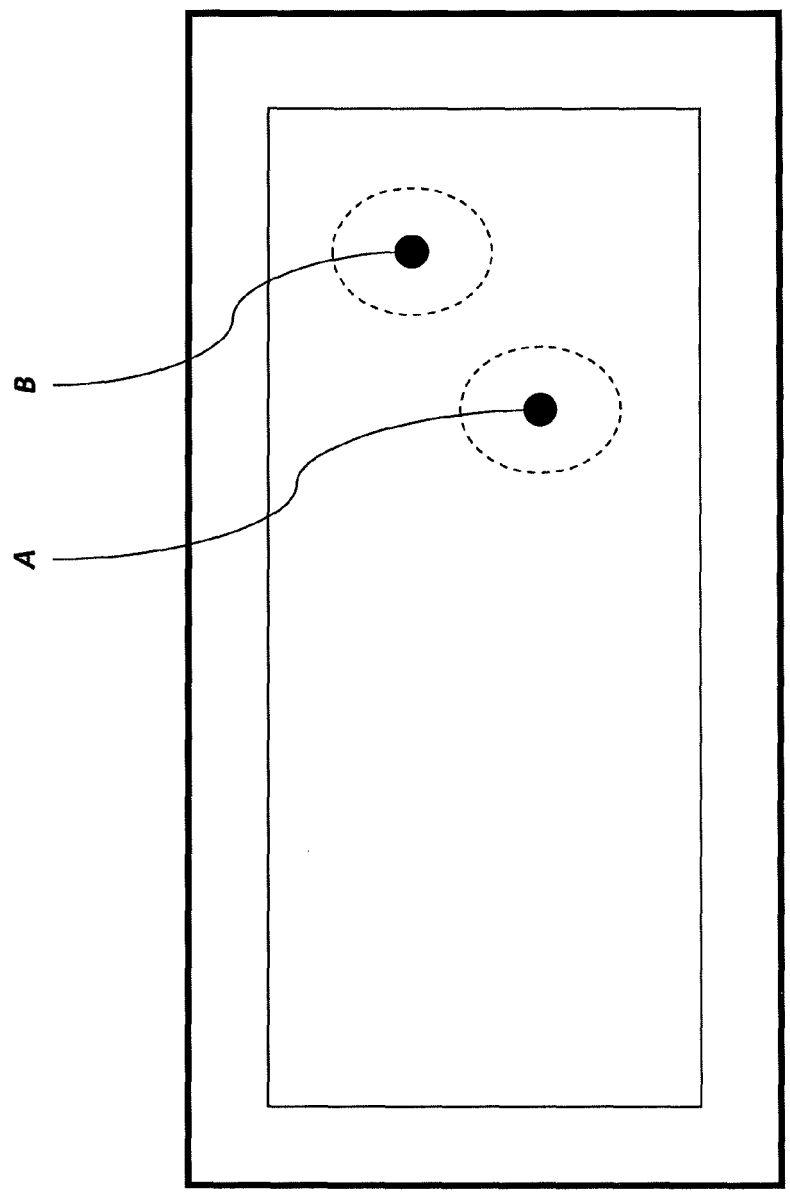
FIGS. 7a and 7b are exemplary SHM/NDE system damage detection software screen shots.
Figure 7B:
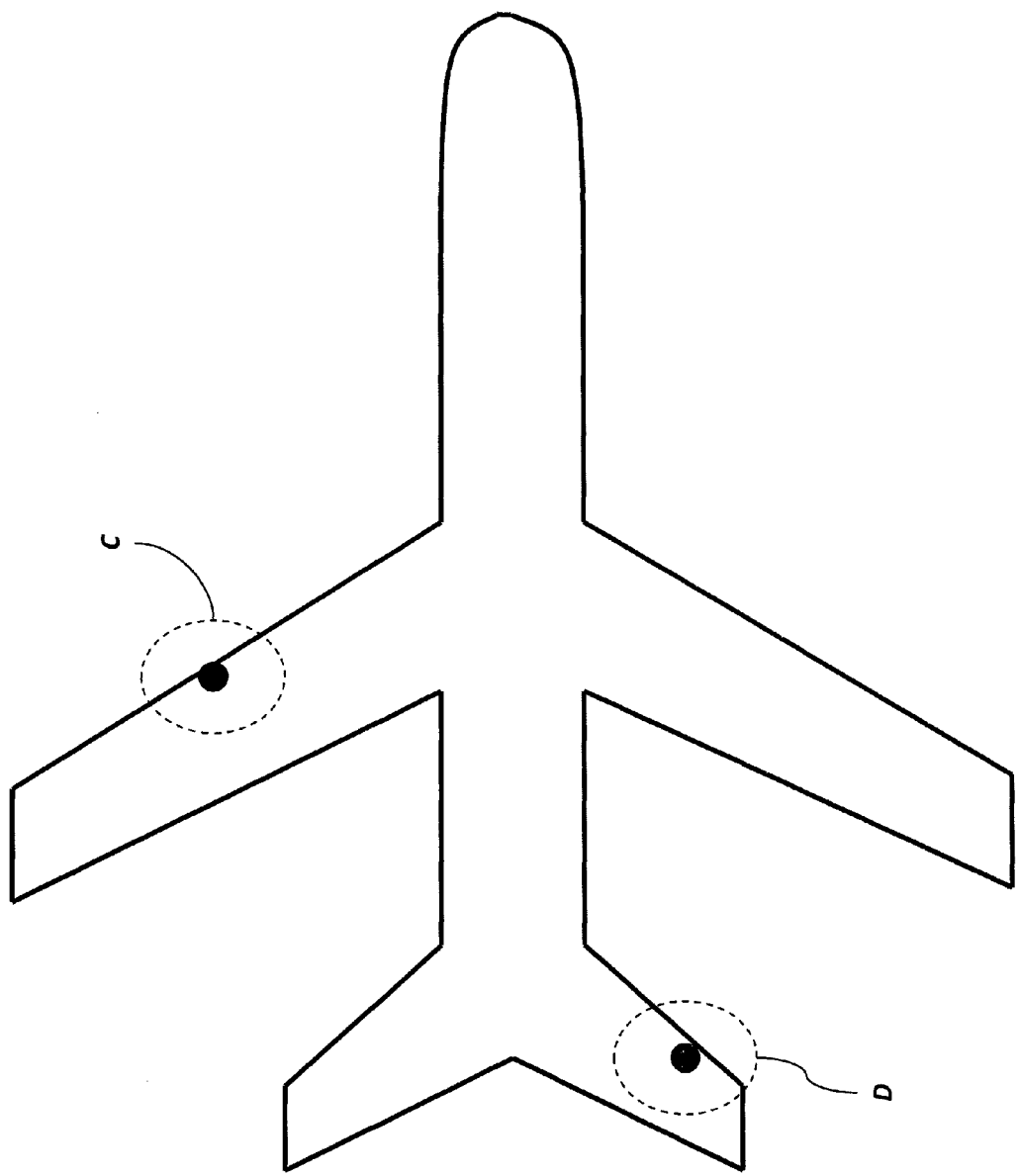

FIGS. 7a and 7b are exemplary SHM/NDE system damage detection images that may be displayed in a computer screen shot. SHM software may use visuals to easily notify the user of any measured damage and the location of such measured damage. For example, FIG. 7a may be a rectangular-shaped structural component with damage at points A and B. In response to capacitance change, the software running on the computer may display a visual representation of the component with marks to indicate the location and severity of damage (circles at points A and B). FIG. 7b illustrates another possible visual that may be displayed in a computer screen shot. To monitor the components of an entire aerial vehicle, an outline of the aerial vehicle (e.g., an aircraft) may be displayed with marks to indicate the location and severity of damage (circles at points C and D). To indicate the level of severity, the indicators (e.g., circles) may be different colors and/or accompanied by a numerical figure to indicate to the user that the damage is, for example, mild, moderate, severe, etc. The computer may also be configured to produce an audible sound to indicate the detection of damage or wear (e.g., once a preset threshold is met) to the pilot or ground personal.

The technology disclosed herein provides maintenance crews with the ability to inspect and evaluate the structural integrity of the airframe components in a cost-efficient way. As previously stated, a significant portion of the current maintenance effort involves inspecting, assessing, and replacing structural components that undergo severe vibration and thermal load cycles. By utilizing a SHM/NDE system, components such as wing ribs, spars and other inaccessible airframe components can be monitored to detect damage that would otherwise be undetectable without large-scale airframe disassembly or teardown. Additionally, the maintenance costs associated with inspections can be reduced through the ability not only to detect but also to locate damage for maintenance crews to perform necessary repairs. The naval applications of this SHM/NDE system could include helicopters and other aircraft, as well as ships and other structures requiring periodic maintenance.

A suitable process for embedding CNT sheets and strands directly into composites for electrical power and signal transfer was developed by Aurora, the assignee of the present application. This embedded CNT system and process provides ingress and egress to the CNT structures without compromising the layered components' structural properties. Aurora also developed methodologies for embedding electrically isolated CNTs into structural components without compromising the structure itself. For further information on CNT embedment, see, for example, commonly owned U.S. Ser. No. 13/020,195 to Robert Parks, entitled "Method and Apparatus for Grounding a Composite Aircraft Structure."

The technology of the present application may be integrated with, or used in conjunction with, for example, the teachings of commonly owned U.S. Ser. No. 12/750,282 to David Kordonowy, entitled "Aircraft Health Monitoring And Design For Condition" (the "'282 application). The '282 application discloses a system and method for automatically varying the flight envelope of an aircraft based upon the material health of the aircraft and the flight environment is provided. The system of the '282 application utilizes a plurality of structural health monitoring and load sensors to determine the approximate size and the approximate location of the damage. The system may also perform residual strength calculations for individual aircraft components to determine the overall aircraft residual strength, which may be used to determine a maximum flight envelope based on the overall aircraft residual strength, and transmits this information to the flight controller and optionally to the pilot.

The individual components shown in outline or designated by blocks in the attached drawings are all well-known in the electrical conductance and aviation arts, and their specific construction and operation are not critical to the operation or best mode for carrying out the invention. While the description so far has centered on use in aviation, it is clear to those of skill in the art that it can be equally applied to other vehicles and vehicular systems, including, for example, automobiles, motorcycles, trains, ships, boats, and spacecraft.

While the present invention has been described with respect to what are currently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

All U.S. and foreign patent documents, all articles, all brochures, and all other published documents discussed above are hereby incorporated by reference into the Detailed Description of the Preferred Embodiment.

What is claimed is:

1. A method for detecting an amount of residual strength remaining in a layered structural component comprising the steps of:

using a layered structural component having embedded conductive layers on at least two opposite surfaces of the layered structural component, wherein said conductive layers are electrically isolated from the layered structural component;

detecting changes in the dielectric of the material between said conductive layers by measuring an electrical capacitance between the conductive layers, by applying a signal waveform to a conductive layer and measuring capacitance rise time;

comparing the measured electrical capacitance to a reference value, wherein deviation from the reference value quantifies an amount of damage in the layered structural component; and correlating the amount of damage in structural integrity to the amount of residual strength remaining in the layered structural component.

2. The method of claim 1, wherein the conductive layers contain material chosen from a group consisting of: (i) carbon nanotubes; (ii) metallic material; (iii) metal mesh; (iv) metalized bondable polymer films; (v) non-metallic electrically conductive material; and (vi) combinations thereof 3. The method of claim 1, wherein the conductive layers are insulated from the layered structural component using a bondable polymer film insulation.

4. The method of claim 1, wherein the conductive layers cover the total surface of the layered structural component.

5. The method of claim 1, wherein each conductive layer comprises multiple strips of conductive material.

6. The method of claim 5, wherein the strips of conductive material on the at least two surfaces of the layered structural component are not parallel, resulting in a grid of strips to allow localization of damage to regions where strips overlap.

7. The method of claim 5, wherein the width of the conductive strips is varied to adjust the resolution of a detectable change in the residual strength remaining.

8. The method of claim 1, wherein each conductive layer comprises multiple layers of conductive material.

9. The method of claim 1, wherein one or more conductive panels cover an area of a first side of the layered structural component and one or more smaller or equal sized conductive panels are used to cover the other side of the same area thereby allowing localization of damage within the area of the smaller damaged conductive panels.

10. The method of claim 9, wherein the area of the smaller conductive panel is varied to adjust the resolution of a detectable change in the residual strength remaining.

11. The method of claim 1, wherein the reference value for a layered structural component is determined after the layered structural component's fabrication but prior to substantial use of the layered structural component, where the reference value is used as a reference point to detect the amount of residual strength remaining.

12. The method of claim 1, wherein the reference value is equal to the capacitance measurement of a reference layered structural component, where the reference value is used as a reference point to detect manufacturing defects.

13. A system for detecting an amount of residual strength remaining in a layered structural component comprising:
conductive layers embedded on at least two opposite surfaces of a layered structural component, wherein said conductive layers are electrically isolated from the layered structural component;
a device for detecting changes in the dielectric of the material between said conductive layers to measure an electrical capacitance by applying a signal waveform to a conductive layer and measuring capacitance rise time;
a monitoring device for comparing the measured electrical capacitance to a reference value, wherein deviation from the reference value quantifies an amount of damage in layered structural component; and
a correlating device for correlating the amount of damage in structural integrity to the amount of residual strength remaining in the layered structural component.

14. The system of claim 13, wherein the conductive layers contain material chosen from a group consisting of: (i) carbon nanotubes; (ii) metallic material; (iii) metal mesh; (iv) metalized bondable polymer films; (v) non-metallic electrically conductive material; and (vi) combinations thereof.

15. The system of claim 13, wherein the conductive layers are insulated from the layered structural component using a bondable polymer film insulation.

16. The system of claim 13, wherein the conductive layers cover the total surface of the layered structural component.

17. The system of claim 13, wherein each conductive layer comprises multiple strips of conductive material.

18. The system of claim 13, wherein each conductive layer comprises multiple layers of conductive material.

19. The system of claim 18, wherein the strips of conductive material on the at least two surfaces of the layered structural component are not parallel, resulting in a grid of strips to allow localization of damage to regions where strips overlap.

20. The system of claim 18, wherein the width of the conductive strips is varied to adjust the resolution of a detectable change in the residual strength remaining.

21. The system of claim 13, wherein one or more conductive panels cover an area of a first side of the layered structural component and one or more smaller or equal sized conductive panels are used to cover the other side of the same area thereby allowing localization of damage within the area of the smaller damaged conductive panels.

22. The system of claim 21, wherein the area of the smaller conductive panel is varied to adjust the resolution of a detectable change in the residual strength remaining.

23. The system of claim 13, wherein the reference value for a layered structural component is determined after the layered structural component's fabrication but prior to substantial use of the layered structural component, where the reference value is used as a reference point to detect the amount of residual strength remaining.

24. The system of claim 13, wherein the reference value is equal to the capacitance measurement of a reference layered structural component, where the reference value is used as a reference point to detect manufacturing defects.

25. A system for detecting an amount of residual strength remaining in a structural component comprising:
a conductive layer sheet located on at least one surface of a structural component, wherein said conductive layer sheet is electrically isolated from the structural component and comprises at least one conductive layer;
a device for detecting changes in the dielectric of the material between said at least one conductive layer and a second conductive layer to measure an electrical capacitance by applying a signal waveform to a conductive layer and measuring capacitance rise time;
a monitoring device for comparing the measured electrical capacitance to a reference value, wherein deviation from the reference value quantifies an amount of damage in the layered structural component; and
a correlating device for correlating the amount of damage in structural integrity to the amount of residual strength remaining in the layered structural component.

26. The system of claim 25, wherein the conductive layer contains material chosen from a group consisting of: (i) carbon nanotubes; (ii) metallic material; (iii) metal mesh; (iv) metalized bondable polymer films; (v) non-metallic electrically conductive material; and (vi) combinations thereof.

27. A method for an amount of residual strength remaining in a structural component comprising the steps of:
placing conductive layers on two opposite surfaces a structural component, wherein said conductive layers are electrically isolated from the structural component;
detecting changes in the dielectric of the component between said conductive layers by measuring an electrical capacitance between the conductive layers by applying a signal waveform to a conductive layer and measuring capacitance rise time;

comparing the measured electrical capacitance to a reference value, wherein deviation from the reference value quantifies an amount of damage in the layered structural component; and correlating the amount of damage in structural integrity to the amount of residual strength remaining in the layered structural component.

28. The method of claim 27, wherein the conductive layers contain material chosen from a group consisting of: (i) carbon nanotubes; (ii) metallic material; (iii) metal mesh; (iv) metalized bondable polymer films; (v) non-metallic electrically conductive material; and (vi) combinations thereof.

* * * * *